US005641773A

United States Patent [19]

Pardee et al.

[11] Patent Number: 5,641,773
[45] Date of Patent: Jun. 24, 1997

[54] METHODS FOR TREATING VIRAL INFECTIONS

[75] Inventors: Arthur P. Pardee, Brookline; Debajit K. Biswas, Newton; Bruce J. Dezube, Newton Centre, all of Mass.

[73] Assignee: Dana-Farber Cancer Institute, Boston, Mass.

[21] Appl. No.: 159,509

[22] Filed: Nov. 30, 1993

[51] Int. Cl.$^6$ .................................... A61K 31/55
[52] U.S. Cl. ................ 514/221; 514/258; 514/262; 514/264
[58] Field of Search ................ 514/221, 264, 514/258, 262

[56] References Cited

U.S. PATENT DOCUMENTS

| | | | |
|---|---|---|---|
| 3,398,159 | 8/1968 | Berger | 260/326.5 |
| 3,400,128 | 9/1968 | Berger | 260/256.4 |
| 3,405,122 | 10/1968 | Berger | 260/239.3 |
| 3,407,211 | 10/1968 | Berger | 260/326.3 |
| 5,036,101 | 7/1991 | Hsu | 514/423 |
| 5,041,438 | 8/1991 | Hsu | 514/221 |

OTHER PUBLICATIONS

Fazely, et al. *Blood* 77:8 (1653–56) Apr. 1991.
Hsu et al. Proc. Natl. Acad. Sci. USA 90(6395–99) Jul. 1993.
Fauci, et al., Science 239:617–622 (1988).
Cullen, et al., Cell 58:423–426 (1989).
Zagury, D., et al. Science 231:850–853 (1986).
Barre–Sinoussi, et al., Science 230:868–871 (1983).
Cox, J.H., et al., Science 247:715–718 (1990).
Levy, J.A., et al., Science 232–*40–842 (1984).
Popovic, M., et al., Science 232:497–500 (1984).
Siegal, F.P., et al, New Eng. Journ. of Medicine, vol. 305, No. 24 pp. 1439–1443 (1981).
Sarngadharan, M.G., et al., Science 224:506–508, (1984).

*Primary Examiner*—Brian M. Burn
*Attorney, Agent, or Firm*—David G. Conlin; Ronald I. Eisenstein

[57] ABSTRACT

The present invention includes, inter alia, methods of treating cells infected with a virus capable of causing an immunodeficiency disease and related pharmaceutical compositions.

17 Claims, 6 Drawing Sheets

METHODS FOR TREATING VIRAL INFECTIONS

BACKGROUND OF THE INVENTION

The human immunodeficiency virus type 1 (HIV-1, also referred to as HTLV-III, LAV or HTLV-III/LAV) and, to a lesser extent, human immunodeficiency virus type 2 (HIV-2) is the etiological agent of the acquired immune deficiency syndrome (AIDS) and related disorders. Barre-Sinoussi, et al., *Science*, 220:868–871 (1983); Gallo, et al, *Science*, 224:500–503 (1984); Levy, et al, *Science*, 225:840–842 (1984); Popovic, et al., *Science*, 224:497–500 (1984); Sarngadharan, et al., *Science*, 224:506–508 (1984); Siegal, et al., *N. Engl. J. Med.*, 305:1439–1444 (1981); Clavel., *AIDS*, 1:135–140 (1987). This disease is characterized by a long asymptomatic period followed by progressive degeneration of the immune system and the central nervous system. Studies of the virus indicate that replication is highly regulated, and both latent and lytic infection of the CD4 positive helper subset of T-lymphocytes occur in the tissue culture. Zagury, et al., *Science*, 231:850–853 (1986). The expression of the virus in infected patients also appears to be regulated as the titer of infectious virus remains low throughout the course of the disease. Both HIV-1 and 2 share a similar structural and functional genomic organization, having regulatory genes such as tat, rev, nef, in addition to structural genes such as env, gag and pol.

While AIDS, itself, does not necessarily cause death, in many individuals the immune system is so severely depressed that various other diseases (secondary infections or unusual tumors) such as herpes, cytomegalovirus, Kaposi's sarcoma and Epstein-Barr virus related lymphomas among others occur, which ultimately results in death. These secondary infections may be treated using other medications. However, such treatment can be adversely affected by the weakened immune system. Some humans infected with AIDS virus seem to live many years with little or no symptoms, but appear to have persistent infections. Another group of humans suffer mild immune system depression with various symptoms such as weight loss, malaise, fever and swollen lymph nodes. These syndromes have been called persistent generalized lymphadenopathy syndrome (PGL) and AIDS related complex (ARC) and may or may not develop into AIDS. In all cases, those infected with the HIV are believe to be persistently infective to others.

The activation of the latent HIV provirus from asymptomatic period has been reported to be governed by long terminal repeats (LTR) in the viral DNA. See Ranki, et al., *Lancet ii*:589–593 (1987); Fauci, et al., *Science*, 239:617–622 (1988); Zaguary, et al, *Science*, 231:850–853 (1985); Mosca, *Nature* (London), 325:67–70 (1987). The activity of HIV-1 is determined by the complex interaction of positive and negative transcriptional regulators that bind to specific sequences within the LTR. Cullen, et al., *Cell*, 58:423–426 (1989). Changes in the quantity or quality of these factors may underlie the activation of transcription of HIV-1 and HIV-2 latent provirus by a myriad of stimuli. See Fauci, *Science*, 239:617–622 (1988); Griffin, et al., *Nature* (London), 339:70–73 (1989); Nabel, et al., *Science*, 239:1299–1302 (1988). Specifically, phorbol 12-myristate-13-acetate (PMA) and Tumor Necrosis Factor-$\alpha$ (TNF$\alpha$) are believed to be potent activators. In particular, TNF$\alpha$ is present in markedly enhanced levels in HIV infected individuals, suggesting that the cytokine plays an important role in the pathogenesis of AIDS. Lahdevirta, *Am. J. Med.*, 85:289–291 (1988).

Most known methods for treating individuals infected with HIV have focused on preventing integration of the virus into the host cells' chromosome or on stages other than dealing with the provirus. Thus, one area of interest has been drugs that affect reverse transcriptase. Many of the proposed therapeutic methods, however, have not proven clinically effective. Indeed, even treatments that have resulted in clinical utility such as AZT (zidovudine) have not been reported to prevent the breakdown of the immune system in many patients after a number of years of treatment. Few methods have been reported to inhibit both expression of integrated provirus and chronic infection of HIV-1. Reverse transcriptase inhibitors, e.g., AZT, ddC, ddI have not been reported to have inhibitory effect on chronic infections.

Another method of treatment that has been proposed is to look for drugs that affect regulatory functions such as tat. The viral switch from latency to active replication requires regulatory protein including tat. The tat protein transactivates regulatory elements in the HIV-LTR and amplifies viral replication many thousand fold. Thus, it has been proposed that by inhibiting tat function, the virus will be stopped or greatly inhibited at the latent stage of viral infection with subsequent replication of the provirus substantially impeded. See, for example, Hsu, et al., U.S. Pat. No. 5,036,101, U.S. Pat. No. 5,041,438, Hsu, *Science* 254:1799–1800 (1992) and Hsu, et al., *Proc. Natl. Acad. Sci. USA*, 90:6395–6399 (1993). 7-chloro-5-(2-pyrryl)-3H-1,4-benzodiazepin-2(1H)-(one) (Ro 5-3335) was considered promising but animal studies revealed some toxicity for Ro 5-3335. An evaluation of 400 analogues resulted in finding 7-chloro-N-methyl-5-(1H-pyrrol-2-yl)-3H-1,4-benzodiaezepin-2 amine (Ro 24-7429) and in the clinical testing of Ro 24-7429. However, this clinical test was stopped.

Another series of compounds has been explored for treating individuals infected by HIV are xanthines. In particular, pentoxifylline (TRENTAL®), Hoechst-Roussel Pharmaceuticals, Inc. Pentoxifylline has been shown to decrease HIV-1 replication in acutely infected peripheral blood mononuclear cells (PBMCs) and in the Jurkat cell line [Fazley, et al., *Blood* 77:1653–1656 (1991)]. Clinical studies have begun with this drug. The present result of the preclinical and clinical study suggests that if there is a role for pentoxifylline in the treatment of AIDS, it will probably be as adjunctive therapy.

Thus, it would be desirable to have a new compound or a combination of compounds that can more effectively inhibit expression or replication of the HIV provirus in HIV infected cells and inhibit chronic infections then currently available. It would also be desirable to be able to effectively administer combinations of drugs at lower cumulative doses than possible currently. It would be particularly desirable to have a new therapy that can be used to treat already infected cells by means of inhibiting expression of provirus, or a means to keep the provirus dormant within infected cells.

SUMMARY OF THE INVENTION

We have now discovered that combinations of drugs that inhibit tat function, i.e. tat inhibitors, and drugs that inhibit NF-κB function work together in a synergistic manner. For example, the use of tat inhibitors such as benzodiazepine compounds and NF-κB inhibitors such as xanthines. One preferred combination includes Ro 24-7429 and pentoxyifylline.

In one embodiment, the combination of compounds can treat cells infected by immunodeficiency viruses, for example, HIV, preferably HIV-1, and thus can be used to treat humans infected by HIV. For example, treatment of those diagnosed as having AIDS as well as those having ARC, PGL and those not yet exhibiting such conditions.

These combinations of compounds can be used against a different target than the conventional drugs being used to treat humans infected by HIV, e.g., reverse transcriptase inhibitors such as zidovudine (AZT), 2',3'-dideoxyinosine (ddI) and 2',3'-dideoxycytidine (ddC). Furthermore, using this combination is anticipated to result in a synergistic result, thus lower dosages may be able to be used. Similarly, the present compounds should be effective in cells that are resistant to reverse transcription inhibitors.

The invention also provides pharmaceutical compositions comprising a combination of the compounds and a suitable carrier therefor for use in the conditions referred to above.

DETAILED DESCRIPTION OF THE INVENTION

Figure 1:
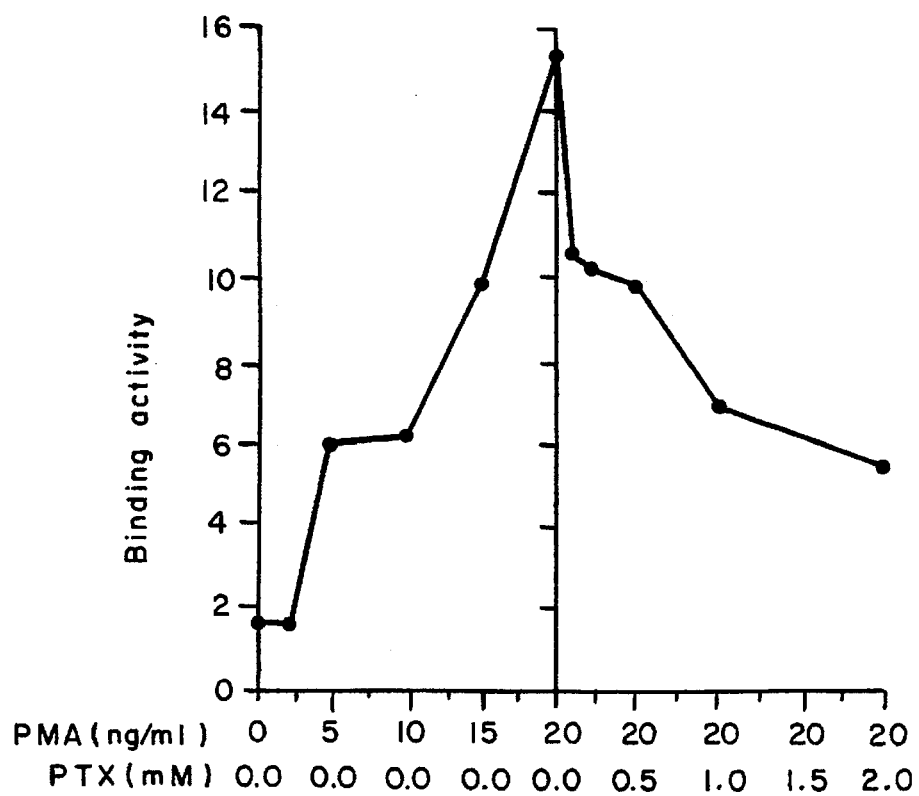
FIG. 1 shows NF-κ binding activity in control and treated cells.

We have discovered that combinations of compounds of the following formula can be used to inhibit expression of an immunodeficiency provirus, for example, to treat cells infected with an immunodeficiency virus such as HIV and thus can be used for treatment in HIV infected individuals.

We have discovered that combinations of compounds that both inhibit different aspects of LTR mediated gene expression work together in a synergistic manner. The effect of LTRs on gene expression in a wide range of immunodeficiency viruses is well-known. For example, in the primate lentiviruses, such as SIV, HIV-1, and HIV-2. This is also true with respect to other immunodeficiency virus, such as feline immunodeficiency virus (FIV), among others. While the primate lentiviruses have varying degrees of sequence homology, they share a strong degree of organizational and functional homology. For example, regulation of immunodeficiency type virus type-1 (HIV-1) and type 2, (HIV-2) gene expression is mediated via interplay of multiple cellular and viral positive (trans-activator) and negative (repressor) factors interacting within small segments of DNA with the long terminal repeat (LTR) sequence [Lu, Y., et al., *Genetic Structure and Regulation of HIV*, Raven Press, NY:415–435 (1991); Gaynor, P., et al., *Genetic Structure and Regulation of HIV*, Raven Press, NY:107–134 (1991)]. These DNA/protein interactions confer specialized gene regulatory properties to the cis-acting elements in the LTR sequence which are essential to effective viral replication. For example, deletions and mutations of specific sites can decrease LTR-driven activation of genes.

Mapping of the LTR by in vitro transcription competition and linker-scanning mutagenesis suggests that specific sequences in the U3-R region (−453 to +80) are necessary for gene regulation [Zeichner, S. L., et al., *J. Virol.* 65:2436–2444 (1991)]. For example, the tat protein plays a major role in trans-activating (stimulating) viral gene expression by interaction with the tar element which is present in this region. Similarly, the nuclear factor NF-κB can also stimulate viral gene expression through its interaction with sequences present in the LTR [Sen, R., et al, *Cell* 47:921–928 (1986); Cullen, B. R., et al., *Microbiol. Rev.* 56:375–394 (1992)]. For example, mutations in the NF-κB response element reduced HIV-1 LTR driven gene expression [Nabel, G. J., et al., *Nature* 326:711–713 (1987); Nabel, G. J., et al., *Science* 239:1299–1302 (1988); Biswas, D. K., et al., *J. Acquir. Immun. Defic. Syndr.* 6:7778–786 (1993)] but do not prevent viral replication [Leonard, J., et al., *J. Virol.* 63:4919–4924 (1989)]. Deletions of this site, together with mutations in the tar element, do render viral replication incompetent. This suggests that concerted action of these two trans-activators plays a role in viral gene regulation and viral replication [Leonard, J., et al., *J. Virol.* 63, supra; Liu, J., et al., *J. Virol.* 66:3883–3887 (1992); Kammine, J., et al., *J. Virol.* 66:3932–3936 (1992); Kadonaga, J. T., et al., *Science* 242:1566–1570 (1988); Doppler, C., et al., *AIDS Res. Hum. Retro. Viruses* 8:245–252 (1992)].

This has lead to various attempts at looking for agents that can affect either of these functions, i.e. tat inhibitors or NF-κB inhibitors. However, to date, the clinical results reported have not been encouraging. We have now surprisingly found that even when using these drugs in combination, one can obtain a synergistic effect. As used herein, the term synergistic means that the effect of the two drugs when used together is greater than their additive effect based upon their use alone would be.

This means that one can obtain a more potent effect using these combinations than using either drug alone. It also means that one can use lower dose levels of these drugs together than one could cumulatively. This is significant as many of these drugs have been shown to have deleterious effects at high levels. For example, clinical tests with pentoxifylline have shown that administration of 400 mg thrice daily is safe and well-tolerated [Dezube, B. J., et al. *JAIDS* 6:787–794 (1993); Sonnabend, J. A., et al., IXth International AIDS Conference, Berlin, Germany, 1:245 Abstract PO-828-0664 (1993); Luke, D. R., et al., *Intl. J. Clin. Pharmacol Toxicol.* 31:343–350 (1993)], but administration of 800 mg thrice daily is not well-tolerated and produces gastrointestinal side effects [Dezube, B. J., et al, IXth International AIDS Conference, Berlin, Germany, 1:492 Abstract No. PO-B28-2142 (1993) and Moll, et al., International AIDS Conference, Berlin, Germany 1:488 Abstract No. PO-B26-2116 (1993)].

Tat inhibitors include those compounds that seek to affect the interaction of a tat protein with the tar element. For example, attempts have been made to use oligonucleotides targeted for inhibition of tat/tar interaction and thereby, HIV-1 LTR-driven gene expression [Vickert, et al., *Nuc. Acids. Res.* 19:3359–3368 (1991)]. More preferably, one would use anti-tat drugs. One series of anti-tat drugs have been described by Hsu, et al. These compounds include aryl-(2-pyrryl) ketone compounds such as 2-glycinamido-5-chlorophenyl (2-pyrryl) ketone and compounds such as benzodiazepine compounds, preferably bezodiazepines. For example, 7-chloro-5-(2-pyrryl)-3H-1,4-benzodiazepin-2 (1H)-one (Ro 5-3335) and 7-chloro-N-methyl-5-(1H-pyrrol-2-yl)-3H-1,4-benzodiazepin-2-amine.

The synthesis of these compounds are disclosed in U.S. Pat. Nos. 5,041,438; 5,036,101; 3,405,122; 3,398,159; 3,407,211; and 3,400,128, all which are hereby incorporated by reference. Ro 24-7429 was synthesized from Ro 5-3335 by reaction with methylamine in the presence of titanium tetrachloride.

Other groupings of compounds that can be used in place of, or in addition to the tat inhibitors disclosed above, include those described in PCT/US93/07878; PCT/US93/07879; and PCT/US93/07934 of which three drugs were reported by Li, et al. [Li, C. J., et al., *Proc. Natl. Acad. Sci. USA* 90:1839–1842] to inhibit LTR function and viral replication. The synthesis of these compounds are described in the above references, all of which are hereby incorporated by reference. Specifically preferred compounds include topotecan, β-lapachone, and allyl-β-lapachone, particularly, 3-allyl-β-lapachone and curcumin.

In cells of non-B-lineage, cytoplasmic NF-κB is detected as a complex with the inhibitory protein, IκB. Thus, phosphorylation of IκB releases NF-κB, which is then translocated into the nucleus, where it interacts with its response element and stimulates HIV-1 LTR-regulated gene expression. Thus, inhibitors of NF-κB may either block the cytoplasmic activation or interfere with the interaction of NF-κB with response elements in the LTR sequence.

Preferably, one uses inhibitors that interfere with NF-κB at the LTR. These include N-acetyl cysteine (NAC) as demonstrated in human embryo kidney cells [Roederer, M., et al., *Proc. Natl. Acad. Sci. USA* 87:4884–4888 (1990); Staal, F. J. T., et al., *Proc. Natl. Acad. Sci. USA* 87:9943–9947 (1990)], cysteine and cysteine derivatives as demonstrated in Molt 4 and U937 cells [Mihm, S., et al., *AIDS* 5:497–503 (1991)], FK506 [S. Schreiber, *Science*, 283–287 (18 Jan. 1991)] as shown in Jurkat cells [Su, M. S., et al., *Transplantation Proceedings* 23:2912–2915 (1991)] and xanthines such as pentoxifylline as shown in human embryo kidney cells [Biswas, D. K., et al., *J. Acquit. Immun. Defic. Syndr.* 6:778–786 (1993)]. One particularly preferred group is xanthines.

One preferred group of xanthines that can be employed in this invention has the following formula:

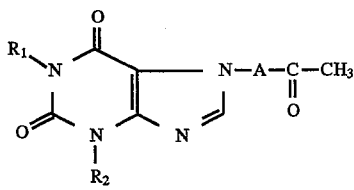
(I)

The substituents $R_1$ and $R_2$ in formula (I) are the same or different and are independently selected from the group consisting of straight-chain or branched alkyl radicals with 2 to 6 carbon atoms, cyclohexyl, alkoxyalkyl, and hydroxyalkyl radicals. The substituent A represents a hydrocarbon radical with up to 4 carbon atoms, which can be substituted by a methyl group.

A preferred compound within formula (I) is 1,3-dibutyl 7-(2-oxopropyl) xanthine. This compound, which is also referred to herein in abbreviated form as "DBOPX", has the following formula:

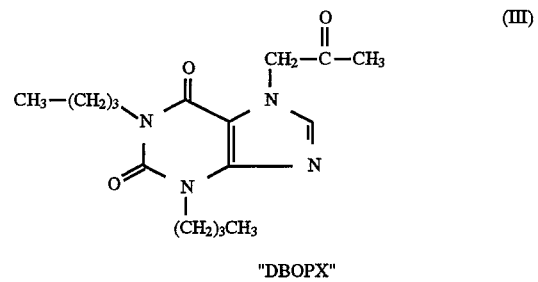

"DBOPX"

The ability of compound (III) to inhibit retroviral activity can be demonstrated.

While DBOPX is the particularly preferred xanthine for use in the invention, a number of other compounds can be employed. For example, the xanthines of formula (I) can be substituted by other alkyl groups, or by alkoxy or hydroxyalkyl groups. Suitable alkyl groups include branched and straight chain groups, such as ethyl, propyl, isopropyl, butyl, sec-butyl, tert-butyl, amyl, hexyl, and the like. Alkoxy substituted alkyl groups include branched and straight combined alkoxy and alkyl groups, including methyoxymethyl, amyloxymethyl, methoxyethyl, butoxyethyl, propoxypropyl, and the like. Hydroxyalkyl groups are those containing from 1 to 6 carbon atoms, such as hydroxymethyl, hydroxethyl, hydroxypropyl, hydroxyhexyl, and the like.

The hydrocarbon groups represented by A in formula (I) are divalent saturated aliphatic hydrocarbon groups, i.e., methylene, ethylene, trimethylene and tetramethylene, which can be substituted on the carbon adjacent the carbonyl group with methyl. Such methyl-substituted groups include ethylidine, 1,2-propylene, and 1,3-butylene groups.

It will be understood that the method of this invention can be practiced with compounds that change in vivo into one of the aforementioned xanthines of formula (I), as well as compounds that produce metabolites in vivo similar to the metabolites formed from the aforementioned xanthines of formula (I).

The compound of formula (I) employed in this invention can be synthesized using known techniques. For example, the compounds can be prepared at elevated temperature, optionally in the presence of a solvent, by reacting correspondingly substituted 1,3-dialkyl xanthines of the formula:

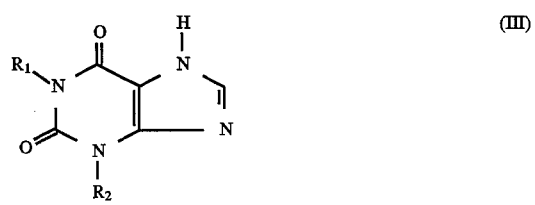
(III)

in which $R_1$ and $R_2$ are as defined above, with α,β-unsaturated methyl ketones corresponding to the formula:

(IV)

The substituent R in formula (IV) represents hydrogen or a methyl group. The reaction can be conducted in an alkaline medium.

An alternative method of preparation involves reacting alkali metal salts of 1,3-dialkyl xanthine derivatives of general formula (I), in which $R_1$ and $R_2$ are as defined above, with oxoalkyl halides corresponding to the formula:

(V)

in which A is as defined above for Formula I, and Hal represents a halogen atom, preferably chlorine or bromine.

These reactions are preferably carried out at temperatures in the range from 40° C. to 80° C., optionally under elevated or reduced pressure, not usually at atmospheric pressure. The individual starting compounds can be employed either in stoichiometric quantities or in excess. The alkali salts in the alternative method of preparation can either be prepared beforehand or in the reaction itself.

Suitable solvents for use in the reactions are water-miscible compounds, preferably lower alcohols, such as methanol, propanol, isopropanol, and various butanols; also acetone; pyridine; triethylamine; polyhydric alcohols, such as ethylene glycol and ethylene glycol monomethyl or monoethyl ether.

The compounds of formula (I) are known for their marked effect in increasing blood flow through the skeletal muscle and by their low toxicity. The most active of these compounds for use in accordance with the present invention is 1,3-dibutyl 7-(2-oxopropyl)xanthine, i.e., DBOPX.

A more detailed description of the compounds employed in this invention and methods of preparing the compounds are contained in U.S. Pat. No. 4,242,345, the entire disclosure of which is relied upon and incorporated by reference herein.

4. Description and Preparation of Xanthines of Formula (II)

Inhibition of human retrovirus activity can also be achieved by administering to a human patient a xanthine of the formula:

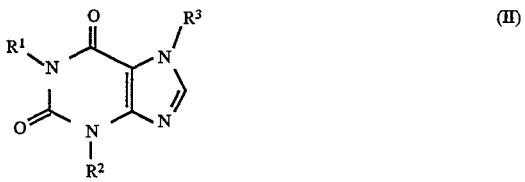
(II)

wherein at least one of $R^1$ and $R^3$ is either (a) a branched hydroxyalkyl group of the formula:

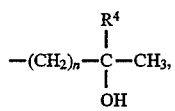

with a tertiary alcohol function, in which $R^4$ stands for an alkyl group with 1 to 3 carbon atoms and n stands for a whole number from 2 to 5, the other $R^1$ or $R^3$ group that may optionally be present stands for a hydrogen atom or an aliphatic hydrocarbon group $R^5$ with up to 6 carbon atoms, whose carbon chain may be interrupted by up to 2 oxygen atoms or may be substituted with a hydroxy or oxo group, or (b) at least one of $R^1$ or $R^3$ is an oxoallyl group of the formula:

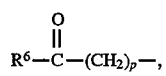

wherein $R^6$ is $C_1$–$C_6$ alkyl, and p=2, 3 or 4; the other $R^1$ or $R^3$ being as defined above, and $R^2$ represents an alkyl group with 1 to 4 carbon atoms. The xanthine of formula (II) is employed in an amount that is effective in inhibiting retroviral activity. Among these compounds is the commercially available compound pentoxifylline (Trental®). A host of other compounds within the general formula (II) can be employed for inhibiting the activity of human retroviruses. Among these compounds are those identified below.

| RETROVIRAL ACTIVITY INHIBITING COMPOUNDS OF FORMULA (II) | | | |
|---|---|---|---|
| COMPOUND NUMBER | $R_1$ | $R_2$ | $R_3$ |
| 2 | $CH_3-\overset{O}{\underset{\|\|}{C}}-$ | $-CH_3$ | $-CH_2-CH_2-CH_3$ |
| 3 | $CH_3-\overset{OH}{\underset{\|}{\underset{CH_3}{C}}}-(CH_2)_4-$ | $-CH_3$ | $-CH_2-CH_2-O-CH_3$ |
| 4 | " | " | $-CH_2-O-(CH_2)_2-O-CH_3$ |
| 5 | " | " | $-H$ |
| 6 | " | " | $-CH_2-CH_2-CH_3$ |
| 7 | " | " | $-CH_2-\overset{OH}{\underset{\|}{CH}}-CH_3$ |

RETROVIRAL ACTIVITY INHIBITING COMPOUNDS OF FORMULA (II)

| COMPOUND NUMBER | R₁ | R₂ | R₃ |
|---|---|---|---|
| 8 | " | " | —CH₂—CH(OH)—(CH₃)₂ |
| 9 | " | —CH₂—CH₃ | —CH₂—O—CH₂—CH₃ |
| 10 | " | —CH₃ | —(CH₂)₄—C(CH₃)(OH)—CH₃ |
| 11 | " | " | —CH₂—O—CH₂—CH₃ |

The compound 7-ethoxymethyl-1-(5-hydroxy-5-methylhexyl)-3-methyl xanthine (HWA448), i.e., Compound No. 11, is also preferred for use in this invention.

It will be understood that the method of this invention can be practiced with compounds that change in vivo into one of the aforementioned xanthines of formula (II), as well as compounds that produce metabolites in vivo similar to the metabolites formed from the aforementioned xanthines of formula (II).

For example, after oral and intravenous administration, pentoxifylline is almost completely metabolized. The following seven metabolites have been identified in human urine, which is the predominant pathway for excretion of metabolites:

| | |
|---|---|
| Metabolite I | 1-(5-hydroxyhexyl)-3,7-dimethylxanthine |
| Metabolite II | 1-(5,6-dihydroxhexyl)-3,7-dimethylxanthine |
| Metabolite III | 1-(4,5-dihydroxyhexyl)-3,7-dimethylxanthine |
| Metabolite IV | 1-(4,-carboxybutyl)-3,7-dimethylxanthine |
| Metabolite V | 1-(3-carboxypropyl)-3,7-dimethylxanthine |
| Metabolite VI | 1-(5-oxohexyl)-3-methylxanthine |
| Metabolite VII | 1-(5-hydroxyhexyl)-3-methylxanthine |

Metabolites I and V are the major metabolites. Metabolite V, the main urinary Metabolite, accounts for about 50–60 percent of the administered dose. Only traces of pentoxifylline and Metabolite I are found in urine. The dihydroxy derivatives of pentoxifylline (Metabolites II and III) represent approximately 12 percent and Metabolite IV about 8 percent of the excretion products.

The compounds of formula (II) can be prepared according to the disclosure of U.S. Pat. No. 3,737,433 and Belgian Patent No. 831,051 (where $R^1/R^3$ are oxoallyl). For the case where at least one of $R^1/R^3$ is a tertiary alcohol, reference may be had to International Application No. PCT/EP86/00401, filed Jul. 8, 1986, claiming Germany priority of Jul. 8, 1985. This Application addresses, as its invention, a variety of embodiments of synthesis routes for the xanthines of formula (II) embraced in the current invention. All the above references are incorporated herein by reference.

An example of one embodiment consists of
a) reacting 3-alkylxanthines of formula (VII):

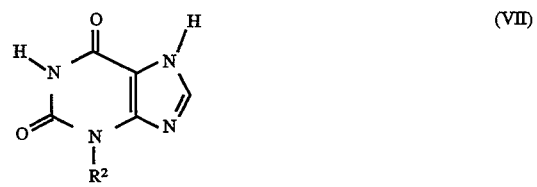

(VII)

in which the $R^3$ represents alkyl with up to 4 carbon atoms, with alkylating agents of formula (VIII):

(VIII)

in which X stands for halogen, preferably chlorine, bromine, or iodine, or a sulfonic acid ester group or a phosphoric acid ester group, and wherein $R^4$ and n have the meanings mentioned above, to obtain compounds of formula (IX):

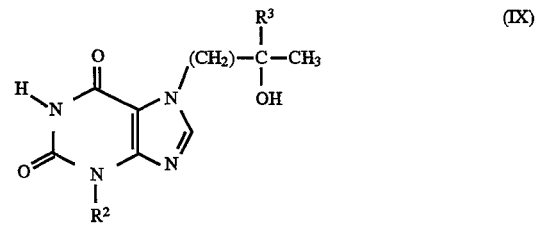

(IX)

with a tertiary hydroxyalkyl group in the position of $R^3$ and hydrogen in the position of $R^1$, and a₁) alkylating this with the same or different alkylating agent of formula (VIII) to obtain compounds pursuant to the invention of formula (X):

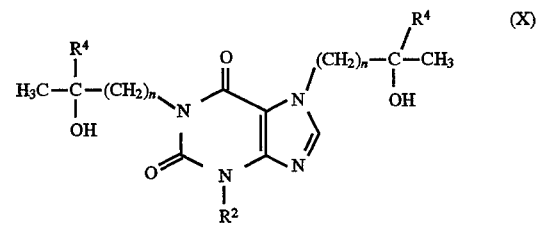

(X)

with two identical or different tertiary hydroxyalkyl groups in the position of $R^1$ and $R^3$, or a₂) converting it with a compound of the formula:

R⁵—X                                                    (Xa)

in which X has the meaning given in formula (VIII) and R⁵ has the meaning indicated above, into compounds of formula (XI):

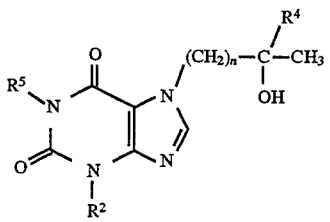

in all cases preferably operating in the presence of basic media or using the xanthines in the form of their salts.

Another embodiment consists of b) substituting 1,3-dialkylated xanthines of formula (XII):

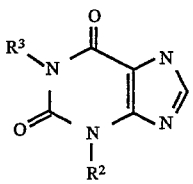

in the 7-position, preferably in the presence of basic media or in the form of their salts, by one-step reaction with a compound of formula (VIII), to obtain the compound of formula (XI).

Another embodiment consists of c) first reacting the 3-alkylxanthines of formula (VII), likewise preferably in the presence of basic media or in the form of their salts, with a compound of the formula:

R¹⁵—X                                                    (XIII)

with the formation of 3,7-disubstituted xanthines of formula (XIV):

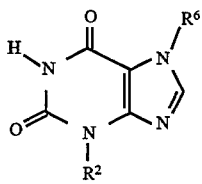

in which R¹⁵ has the meaning mentioned for R⁵ or stands for benzyl or diphenylmethyl, and then substituting them in the 1-position, again preferably in the presence of basic media or in the form of their salts, with a compound of formula (VIII). Compounds of formula (XV) are obtained:

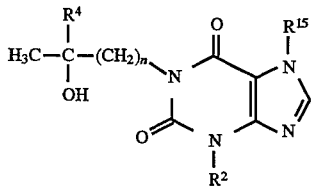

in which R¹⁵ represents a benzyl or diphenylmethyl, and converting the compounds of formula (XV) in which R¹⁵ represents a benzyl or diphenylmethyl group or an alkoxymethyl or alkoxyalkoxymethyl group, under reducing or hydrolytic conditions, into compounds pursuant to the invention of formula (XVI):

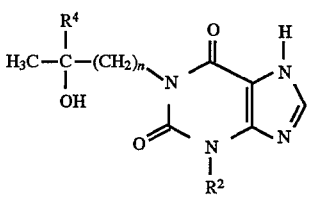

that are subsequently reacted again, if desired, with a compound of formula (VIII) or (Xa) to obtain compounds pursuant to the invention of formula (X) or (XV).

Another embodiment consists of d) reducing compounds of formula (XI) or (XV) pursuant to the invention in which R⁵ or R¹⁵ stands for an oxoalkyl group, with conventional reducing agents for the keto group to obtain the corresponding hydroxyalkylated xanthines pursuant to the invention.

The 3-alkyl- or 1,3-dialkylxanthines of formula (VII) or (XII) used here as starting materials and the "alkylating agents" of formula (VIII), (Xa) and (XIII) are known for the most part or can be prepared readily by methods disclosed in the literature. Thus, the tertiary alcohols of formula (VIII), for example, can be obtained by organometallic synthesis by reacting the sterically unhindered haloketones of the formula:

Hal—(CH₂)ₙ'CO—CH₃                                       (XVII)

in a so-called synthetic reaction with reductive alkylation of the carbonyl group, with alkylmetal compounds R⁴—M, especially of magnesium, zinc, or lithium, for example in the form of alkylmagnesium halides R⁴—MgHal (Grignard compounds) or of the alkyllithium compounds R⁴—Li, under the usual conditions (for example, see Houben-Weyl, Vol. VI/1 a, Part 2 (1980), pp. 928–940, especially pp. 1021 ff. and 1104–1112). In the same way, a reaction of the haloketones with the formula:

Hal—(CH₂)ₙ—CO—R⁴                                        (XVIII)

with methylmagnesium halides or methyllithium likewise leads to the target.

The hydroxyketones corresponding to the formulas (XVII) and (XVIII) can also be converted smoothly into diols with the alkylmetal compounds in the usual way, either directly or with temporary masking of the hydroxy group, for example by acetal formation with 5,6-dihydro-4H-pyran (for example, see Houben-Weyl, Vol. VI/1 a, Part 2 (1980), pp. 1113–1124), from which compounds of formula (VIII) are formed by selective esterification of the terminal primary hydroxyl groups with sulfonyl or phosphoric halides or anhydrides, advantageously in the presence of basic media.

Other possibilities for the synthesis of the tertiary alcohol derivatives of formula (VIII) consist of the monometallation of ω-chloro-1-bromooalkanes to obtain ω-chloroalkylmetal compounds, (Houben-Weyl, Vol. XIII/2 a (1973), pp. 102 and 319) and their subsequent reaction with the ketones R⁴—CO—CH₃, with the extent of by-product formation from the alkanolates formed as intermediates because of their tendency toward ring closure with the elimination of metal salt being minimized by appropriate temperature control, or of using ω-halo-1-alkanols as starting materials, which are metallated in the usual way, preferably in the form of the tetrahydropyranyl-(2) ether or after alkanolate formation of the hydroxy group (MO—CH₂)ₙ—Hal) with any desired alkylmetal compound (for example, see Houben-Weyl, Vol. XIII/2 a (1973), p. 113), then reacting them with the ketones R⁴—CO—CH₃ to obtain the diols mentioned in the preceding paragraph (Houben-Weyl, Vol. VI/1 a, Part 2 (1980), p. 1029), and subsequently selectively esterifying the primary hydroxy group with suitable sulfonic or phosphoric acid derivatives.

A convenient access to compounds of formula (VIII) in which $R^4$ represents a methyl group is also available through a reaction of ω-haloalkanoic acid alkyl esters (Hal—(CH$_2$)$_n$—COO-alkyl) with two equivalents of a methylmetal compound, with the ester reacting through the ketone to produce the tertiary alcohol with the introduction of two methyl groups (Houben-Weyl, Vol. VI/1 a, Part 2 (1980), pp. 1171–1174). In the same way, ω-hydroxy-carboxylic acid esters can be converted into diols with methylmetal compounds with or without protection of the hydroxy group, for example, in the form of tetrahydropyranyl-(2) or methoxymethyl ester, or optionally in the form of the lactones as cyclic esters (for example, see Houben-Weyl, Vol. VI/1 a, Part 2 (1980), pp. 1174–1179), from which active alkylating agents of formula (VIII) can in turn be obtained by selective esterification of the primary hydroxyl group with sulfonic or phosphoric halides or anhydrides.

Suitable compounds of formula (VIII) that can be prepared by the methods described above are thus the [(ω-1)-hydroxy-((ω-1)-methyl]butyl, -pentyl, -hexyl, and heptyl, the [ω-2)-hydroxy-(ω-2)-methyl]pentyl, -hexyl, -heptyl, and octyl, and the [ω-3)-hydroxy-(ω-3)-methyl]hexyl, -heptyl, octyl, and -nonyl chlorides, bromides, iodides, sulfonates, and phosphates.

Among the compounds of formula $R^5$—$X_5$ (Xa) or $R^{15}$—X (XIII) suitable for the introduction of $R^5$ into the 1- or 7-position and of $R^{15}$ into the 7-position of the xanthine skeleton, the alkoxymethyl and alkoxyalkoxymethyl derivatives occupy a special position as their halides can indeed be used successfully as reactants, but toxicological problems can arise, at least in large-scale use. For this reason, the use of the corresponding sulfonates is preferred in this special case, which are readily available, for example, by reacting mixed anhydrides of aliphatic carboxylic acids and aliphatic or aromatic sulfonic acids (M. H. Karger, et al., *J. Org. Chem.*, 36:528–531 (1971)) with the formaldehyde dialkyl acetals or dialkoxyalkyl acetals in a smooth and nearly quantitative reaction (M. H. Karger, et al., *J. Amer. Chem. Soc.*, 91:5663–5665 (1969)):

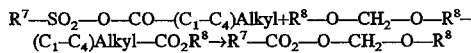

In this equation, $R^7$ represents an aliphatic group such as methyl, ethyl, or trifluoromethyl, or an aromatic group, for example, phenyl, 4-tolyl, or 4-bromophenyl, but preferably methyl or 4-tolyl, and $R^8$ represents an alkyl or alkoxyalkyl group falling under the definition of $R^5$ or $R^{15}$.

The reaction can be carried out either in the substance or in an anhydrous aprotic solvent inert to the reactants at temperatures between −20° C. and +40° C., preferably between 0° C. and 20° C. No intermediate isolation of the highly reactive sulfonates, which are sensitive to hydrolysis and thermally labile, is necessary; they are preferably used immediately as crude products for the substitution on the nitrogen of the xanthines, with the usual addition of a basic condensing agent being unnecessary.

The reaction of the mono- or disubstituted xanthine derivatives, (IX), (XVI), (VII), (VIII) or (Xa) or (XIII) is ordinarily done in a distributing agent or solvent inert to the reactants. Practical representatives are especially dipolar, aprotic solvents, for example, formamide, dimethylformamide, dimethylacetamide, N-methylpyrrolidone, tetramethylurea, hexamethylphosphoric triamide, dimethyl-sulfoxide, acetone, or butanone; however, alcohols such as methanol, ethylene glycol, and their mono- or dialkyl esters with the alkyl group having 1 to 4 carbon atoms but both together having a maximum of 5 carbon atoms, ethanol, propanol, isopropanol, and the various butanols; hydrocarbons such as benzene, toluene or xylenes; halogenated hydrocarbons, such as dichloromethane or chloroform; pyridine, and mixtures of the solvents mentioned or their mixtures with water can also be used.

The "alkylation reactions" are suitably carried out in the presence of a basic condensing agent. Examples of materials suitable for this are alkali metal or alkaline earth hydroxides, carbonates, hydrides, alcoholates, and organic bases, such as trialkylamines (for example, triethyl- or tributylamine), quaternary ammonium or phosphonium hydroxides and crosslinked resins with fixed, optionally substituted ammonium or phosphonium groups. The xanthine derivatives can also be used in the alkylation reaction directly in the form of their separately prepared salts, such as the alkali metal, alkaline earth, or optionally substituted ammonium or phosphonium salts. The mono- and disubstituted xanthine derivatives can also be alkylated either in the presence of the aforementioned inorganic condensing agents or in the form of their alkali metal or alkaline earth salts with the assistance of so-called phase transfer catalysts, for example, tertiary amines, quaternary ammonium or phosphonium salts, or crown ethers, preferably in a 2-phase system under the conditions of phase transfer catalysis. Among the suitable phase transfer catalysts that are generally commercially available are tetra ($C_1$–$C_4$)alkyl- and methyltrimethylammonium and -phosphonium salts, methyl-, myristyl-, phenyl-, and benzyltri ($C_1$–$C_4$)-alkyl- and acetyltrimethylammonium as well as ($C_1$–$C_{12}$)alkyl- and benzyltriphenylphosphonium salts, with the compounds that have the larger and more symmetrically structured cation generally proving to be the more effective.

The introduction of the groups Ia, $R^5$, and $R^{15}$ by the procedures described above is generally carried out at a reaction temperature between 0° C. and the boiling point of the particular reaction medium used, preferably between 20° C. and 130° C., optionally at elevated or reduced pressure, for which the reaction time can amount to less than 1 hour or up to several hours.

The reaction of the 3-alkylxanthines (VIII) to produce the compounds pursuant to the invention of formula (X) requires the introduction of two tertiary hydroxyalkyl groups. Either identical or different substituents can be linked to the xanthine skeleton in succession, or two identical hydroxyalkyl groups can be linked without isolation of intermediates in a single-pot reaction.

The reductive cleavage of the benzyl and diphenylmethyl group from compounds of formula (XV) with the formation of the xanthine atom in the 7-position, is carried out under standard conditions that were developed especially in the framework of the protective group technique in alkaloid and peptide synthesis and can thus be assumed to be widely known. Besides the chemical reduction, particularly of the benzyl compounds with sodium in liquid ammonia (Houben-Weyl, Vol. XI/1 (1957), pp. 974–975), the elimination of the two aforementioned aralkyl groups by catalytic hydrogenolysis using a precious metal catalyst is also especially practical (Houben-Weyl, Vol. XI/1 (1957), pp. 968–971 and Vo. IV/1 c, Part I (1980), pp. 400–404). A lower alcohol is ordinarily used here as the reaction medium (optionally with the addition or formic acid or ammonia), or an aprotic solvent such as dimethylformamide or particularly glacial acetic acid; however, their mixtures with water can also be used. Especially suitable hydrogenation catalysts are palladium black and palladium on activated charcoal or barium sulfate, while other precious metals such as platinum, rhodium, and ruthenium frequently give rise to side reactions because of competitive ring hydrogenation and are therefore only conditionally usable. The hydrogenolysis is preferably carried out at temperatures between 20° C. and 100° C. and at atmospheric pressure, or preferably slight excess pressure up to approximately 10 bar, with reaction times of a few minutes to several hours generally being needed.

The 1,3,7-trisubstituted xanthines of formula (XV) that have an alkoxymethyl or alkoxyalkoxymethyl group in the position of $R^{15}$ represent O,NB-acetals. Consequently, their substituents in the 7-position can be split off under the usual conditions of acid hydrolysis (cf. Houben-Weyl, Vol. VI/1 b (1984), pp. 741–745), with the 7H compounds of formula (XVI) likewise being formed. Examples of preferred groups that can be eliminated hydrolytically are the methoxy, ethoxy and proproxymethyl groups as well as the methoxyethyoxy- and ethoxyethoxymethyl groups. The reaction is advantageously carried out with heating in dilute mineral acids such as hydrochloric or sulfuric acid, optionally with the addition of glacial acetic acid, dioxane, tetrahydrofuran, or a lower alcohol as a solution promoter. Also useful are perchloric acid or organic acids, such as trifluoroacetic, formic, and acetic acids, in combination with catalytic amounts of mineral acids. The alkoxyalkoxymethyl compounds in particular can also be cleaved by using Lewis acids, such as zinc bromide and titanium tetrachloride in anhydrous medium, preferably in dichloromethane or chloroform, with the 7-bromomethyl or 7-bromozinc derivatives formed as intermediates hydrolyzing spontaneously during the aqueous workup. In the cleavage in mineral acid solution, the reaction temperature must be chosen so that no significant dehydration of the tertiary hydroxyalkyl group in the 1-position occurs; it should therefore be below 100° C. as a rule.

The reduction of the xanthines of formulas (XI) and (XV) with oxoalkyl group in the position of $R^5$ and $R^{15}$ to the corresponding hydroxyalkyl compounds can indeed take place in principle either with base metals or by catalytic hydrogenation, but the method of choice consists of the reaction occurring under very mild conditions and in high yields with simple metal hydrides ($MH_n$), complex metal hydrides ($M^1[M^2H_n]_m$), or organometallic hydrides (Houben-Weyl, Vol. IV/1 d (1981), pp. 267–282, and Vol. VI/1 b (1984), pp. 141–155). Of the numerous complex metal hydrides that can be used for the reduction of ketones, the most frequently used reagents might be mentioned, for example, lithium alanate, lithium borohydride, and especially sodium borohydride, that is easier to handle because of its lower reactivity and above all permits working in alcoholic, alcoholic aqueous, and pure aqueous solutions or suspensions. In addition to the otherwise customary inert solvents, such as ethers (for example, diethyl ether, tetrahydrofuran, 1,2-dimethoxyethane), hydrocarbons and pyridine, nitriles, such as acetonitrile, can also be used as the reaction medium. The hydrogenation, which is suitably carried out at temperatures between 0° C. and the boiling point of the particular solvent, but preferably at room temperature, generally occurs rapidly and is complete within several minutes to a few hours.

The tertiary hydroxyalkylxanthines of formula (II) can also be prepared by reacting substituted xanthines of formula (XIX):

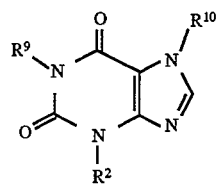

e) contains two identical or different groups of the formula:

$$-(CH_2)_n-CO-CH_3 \qquad (XX); or$$

$$-(CH_2)_n-CO-R^4 \qquad (XXI)$$

or only one substituent of the formula (XX) or (XXI), and hydrogen or the group $R^5$ or $R^{15}$ in the positions of $R^9$ and $R^{10}$, with $(C_1-C_3)$alkyl- or methylmetal compounds with reductive "alkylation" of the carbonyl groups to obtain the xanthines pursuant to the invention of formulas (IX) to (XVI), or f) metallating xanthines of formula (XIX) that have two identical or different groups of the formula $-(CH_2)_n-Hal$ (XVII), with Hal preferably standing for chlorine or bromine or only one such group and hydrogen or the substituent $R^5$ or $R^{15}$ in the other position, in the terminal position, and then reacting them with the ketones of the formula:

$$R_4-CO-CH_3 \qquad (XVIII)$$

with reductive alkylation of the carbonyl group to obtain the xanthines of formulas (IX) to (XVI) pursuant to the invention, or g) converting xanthines of formula (XIX) with the group:

$$-(CH_2)_n-COO-(C_1-C_4)\text{-alkyl} \qquad (XXIV)$$

in the positions of $R^9$ and/or $R^{10}$ and optionally hydrogen or the group $R^5$ or $R^{15}$ in the other position, by means of two equivalents or a methylmetal compound per alkoxycarbonyl group, into xanthines of formulas (IX) to (XVI) in which $R^4$ stands for methyl, or h) converting xanthines of formula (XIX) having two identical or different groups of the formula:

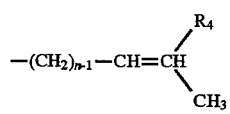

or only one such group and hydrogen or the group $R^5$ or $R^{15}$ in the position of $R^9$ and $R^{10}$, in which the group (XXV) can contain the C=C double bond also in position-isometic arrangements on the branched carbon atom, for example, as $-C=CH_2$, by acid-catalyzed hydration obeying the Markownikoff Rule, into the xanthines of formula (IX) to (XVI) pursuant to the invention, and if desired, then converting the tertiary hydroxaly-xanthines of formulas Ib$^1$ and if obtained pursuant to the invention by methods (e to h) that have a hydrogen atom in the 1- or 7-position, optionally in the presence of basic media or in the form of their salts, with the alkylating agents of formula (VIII) or (Xa) or (XIII), into the trisubstituted compounds of formulas (X) or (XI) or (XV), in which $R^2$, $R^4$, $R^5$, $R^{15}$, and n in the formulas above have the meanings indicated above.

The 3-alkylated mono- or dioxoalkyl-(XIXa), -(ω-haloalkyl) (XIXb), -(ω-alkoxycarbonylalkyl)-(XIXc), and -alkenylxanthines (XIXd) needed for this as starting materials are either known or can be prepared readily, for example, from the 3-alkyl-xanthines (VII) and the sulfonyloxy- or haloketones (XVII) and (XVIII), ω-haloalkylsulfonates, or 1,ω-dihaloalkanes (c.f., for example: V. B. Kalcheva, et al., *Journal fur prakt. Chemie* 327:165–168 (1985)), ω-sulfonyloxy or ω-halocarboxylic acid alkyl esters or sulfonyloxy or haloalkenes corresponding to formula (XXV) under the reaction conditions previously described in detail for the alkylation of mono- and disubstituted xanthines with the compounds of formulas (VIII) and (Xa).

In the organometallic reactions of the xanthines (XIXa) and (XIXc) functionalized in the $R^9$ and $R^{10}$ groups, the procedure is the same in principle as described for the preparation of the tertiary alcohols of formula (VIII) used as alkylating agents. Thus, the reductive alkylation of the ketones (XIXa) and of the esters (XIXc) can take place, for example, with alkylpotassium, -sodium, -lithium, -magnesium, -zinc, -cadmium, -aluminum, and -tin compounds. The recently recommended alkyltitanium and -zirconium compounds (D. Seebach, et al, *Agnew Chem.*, 95:12–26 (1983)) can also be used. However, since the alkylmetal compounds of sodium and potassium have a tendency toward side reactions because of their high reactivity and those of zinc and cadmium are relatively sluggish, the alkyllithium and -magnesium (Grignard) compounds are ordinarily preferred.

The strong nucleophilic organometallic compounds are very sensitive to hydrolysis and oxidation. Their safe handling therefore requires working in anhydrous medium, optionally under an inert gas atmosphere. The usual solvents or distributing agents are primarily those that are suitable also for the preparation of the alkylmetal compounds. Practical examples are especially ethers with one or more ether oxygen atoms, for example, diethyl, dipropyl, dibutyl, or diisomyl ether, 1,2-dimethoxyethane, tetrahydrofuran, dioxane, tetrahydropyran, furan, and anisole, and aliphatic or aromatic hydrocarbons, such as petroleum ether, cyclohexane, benzene, toluene, xylenes, diethylbenzenes, and tetrahydronaphthalene; however, tertiary amines, such as triethylamine, or dipolar aprotic solvents, such as hexamethylphosphoric triamides, as well as mixtures of the solvents mentioned can also be used successfully. The reaction of the carbonyl compounds (XIXa) and (XIXc) with the Grignard compounds with the formula $R^4$—MgHal can also beneficially be carried out by placing the organometallic compound in an ether and adding the ketone or the ester dropwise as a solution in dichloromethane or 1,2-dichloroethane. An addition of magnesium bromide is frequently recommended, which is able to increase the nucleophilicity of the organometallic compound because of its participation in the complex cyclic transition state.

The ketone or ester and the organometallic compound are generally combined at temperatures between −20° C. and 100° C., preferably between 0° C. and 60° C., or at room temperature without external cooling, with the alkylmetal compound ordinarily being used in slight excess. The reaction is then ordinarily completed by brief heating under reflux, for which times of several minutes to a few hours are generally adequate. The alkanolate formed is preferably decomposed with aqueous ammonium chloride solution or dilute acetic acid.

Metallic magnesium and lithium are primarily suitable for the metallation of the ω-haloalkylxanthines (XIXb). On the other hand, the replacement of the halogen atom with lithium, which is also possible using organolithium reagents, generally 1-butyl-, 2-butyl-, t-butyl-, or phenyllithium, plays a subordinate role. However, use is made especially of the Grignard compounds, advantageously preparing them in the ethers, hydrocarbons, tertiary amines, or aprotic solvents listed as particularly suitable for the reaction of the xanthines (XIXa) and (XIXc) with alkylmetal compounds at temperatures between 25° C. and 125° C., preferably below 100° C. If the metallation reaction is carried out as hydrocarbons, then the addition of an ether, such as tetrahydrofuran, or as tertiary amine, such as triethylamine, in stoichiometric amount frequently proves useful. The use of catalysts, such as butanol, aluminum chloride, silicon tetrachloride, tetrachloromethane, and aluminum or magnesium alcoholates, may also be helpful. In the halogen-metal exchange the chlorides ordinarily react more slowly than the corresponding bromides and iodides, but as a rule they provide better yields of organometallic compound. To accelerate the beginning of the reaction, the addition of some magnesium bromide, some grains of iodine, or several drops of bromine, tetrachloromethane, or methyl iodide with slight heating is frequently recommended. The Grignard compounds obtained are normally not isolated, but are reacted immediately with the ketones of formula (XXIII) under the reaction conditions described for the reductive alkylation of the xanthines (XIXa) and (XIXc).

The addition of water to the C=C double bond of the alkenylxanthines (XIXd) with the structural element of formula (XXV), in which the hydroxy group adds to the carbon atom with the fewer hydrogens to form tertiary alcohols according to the Markownikoff Rule, ordinarily occurs in aqueous solution or suspension in the presence of strong acids, such as sulfuric, nitric, or phosphoric acid. Hydrogen halides and sulfonic acids, such as trifluoromethanesulfonic acid, acid exchange resins, boron trifluoride complexes, or oxalic acid, can also be used as catalysts. However, it is preferred to operate in sulfuric acid, with an acid concentration of 50 to 65% and temperatures of 0° C. to 10° C. being sufficient as a rule. However, lower or higher acid concentration and/or reaction temperatures can sometimes also be used. In any case, the reaction temperatures should be kept as low as possible since the reverse dehydration to the olefin can be disturbingly significant above approximately 60° C.

The addition of a solvent inert to acids, such as 1,4-dioxane, benzene, or toluene, sometimes also provides benefits. Since esters can form as intermediates in the acid-catalyzed hydration, particularly when using the high acid concentrations, it is recommended to treat the reaction batch with a large amount of water with brief heating after the action of the acid for the purpose of ester hydrolysis, or to process the mixture in the alkaline range.

The experimental conditions for the optional conversion of the 1- and 7H-compounds (IX) or (XVI) pursuant to the invention into the trisubstituted xanthines of formulas (X) or (XV) by N-alkylation with the compounds (VIII) or (Xa) of (XIII) have already been described above in detail.

Depending on the chain length of the alkyl group $R^4$ (at least $C_2$) and/or the structure of a substituent $R^5$ (for example, 2-hydroxypropyl), the tertiary hydroxyalkylxanthines of formula (II) can have one or two asymmetric carbon atoms and can thus be present in the stereoisomeric forms. This invention therefore concerns both the pure stereoisomeric compounds and their mixtures.

Preferred xanthines for use herein include the xanthines of formula II, and preferably include 1,3-di-methylxanthine (theophylline), 1-(5-oxohexyl)-3,7-dimethylxanthine (pentoxyfylline), 1-(5-hydroxy-5-methylhexyl)-3-methylxanthine) (HWA 138), 7-ethoxymethyl-1-(5- hydroxy-5-methylhexyl)-3-methylxanthine (HWA 448) and 7-propyl-1-(5-hydroxy-5-methylhexyl)-3 methylxanthine (A80 2715). More preferably, one uses pentoxyfylline, BL 194, HWA 138, HWA 448 or A80 2715. Even more preferably one use pentoxifylline, HWA 138 or HWA 448. Still more preferably, one would use pentoxyfylline.

The combination of compounds described provide more effective therapy of chronically infected cells as evidenced by a reduction in, preferably a complete repression of, HIV LTR directed gene expression. Thus, in an HIV infected cell addition of an effective amount of a compound of the combination will reduce the expression of a gene operably linked to the HIV LTR by use of lower amounts of the two drugs together than can be achieved by either drug alone. Preferably, the gene is operably linked to an HIV-1 LTR. As used herein, the term operably linked means that the gene is under the control of the HIV LTR and positioned in a nucleotide sequence in a way to accomplish this. Typically, the gene is downstream of the LTR, which acts as a promoter. Preferably, the gene corresponds to a viral gene such as the HIV env gene, HIV rev gene, etc.

Hence, in one preferred embodiment, the present invention can be used in treating those diagnosed as having AIDs as well as those having ARC, PGL, and those seropositive but asymptomatic patient. For example, as a preventative, it can also be used prophylactically as a preventative for high risk individuals. This, method of protection comprised administering an effective amount of the combination by means as set forth below.

The combinations disclosed herein can be used to treat cells, especially mammalian cells and in particular human cells, infected by an immunodeficiency virus such as HIV infected cells. As a result of treatment with the combination of viral expression is significantly reduced. Furthermore, one can use lower dosages. Thus, side effects such as seen with high levels, such as 800 mg of pentoxifylline at thrice daily administration can be avoided. Similarly, compounds such as Ro 5-3335 which have unacceptable toxicity when used alone can be reevaluated. Further, compounds such as Ro 24-7429, which by itself was not considered clinically effective, can be used in combination.

For example, viral expression of HIV can be studied by a number of methods such as looking at the expression of a marker gene, e.g., CAT lacZ, etc., operably linked to the HIV LTR, which acts as the promoter. Use of the present combination of compounds such as pentoxifylline and Ro 24-7429 can significantly reduce expression of such a marker. HIV-1 viral expression is turned on and enhanced by HIV LTR stimulators such as tumor necrosis factora (TNFα) or phorbol-12-myristate-13-acetate (PMA). One product of this expression, i.e., tat can further augment HIV-1 gene expression. Using a marker gene such as chloramphenicol acetyl transferase (CAT) operably linked to the HIV LTR in HIV infected cells, the addition of an effective amount of the presently described of combination compounds significantly inhibits expression of gene, thereby indicating that HIV expression under the control of the HIV LTR such as HIV envelope glycoprotein expression would be inhibited if not completely stopped.

$P^{24}$, a major structural protein (product of gag), has been widely used for monitoring HIV-1 replication in cells and viraemia in individuals. Use of the present combination of compounds, at concentrations that do not significantly adversely affect cells, should dramatically reduce HIV-1 replication, as determined by $P^{24}$ levels, i.e., preferably a reduction of more than 25% as determined by $P^{24}$ levels, more preferably a reduction of more than 50%, and still more preferably a reduction of HIV-1 replication of more than 80% as determined by $P^{24}$ levels.

The effective amount used to obtain such a result will be at lower levels than those cumulatively used, preferably at micromolar and even more preferably at nanomolar concentrations. For example, it is believed that one can reduce the cumulative dosage level of constituents by at least 20%, more preferably at least 25%, even more preferably at least 50%, still more preferably by at least 70%, and most preferably at least 90%. Furthermore, the administration of the combination of compounds of the present invention at effective concentrations, which inhibit, for example, HIV expression, do not adversely effect the cell.

The compounds of the present invention can be administered to HIV infected individuals or to individuals at high risk for HIV infection. For example, those having sexual relations with an HIV infected partner, intravenous drug users, etc. Because of its inhibitory effect, the combination of compounds of the present invention can be used prophylactically as a method of prevention for such individuals to minimize their risk. One would administer an effective amount of the combination as set forth below by the methodology described herein.

As demonstrated in the Examples which follow, the combination compounds described block activation or suppress activity of HIV-1 LTR at a synergistic level when compared to either component by itself, and thus expression of genes under its control in both chronically and acutely infected cells. In particular, it has been found that combinations in a dose dependent fashion inhibit HIV LTR directed TNFα and PMA stimulated gene expression. Moreover, such inhibition is provided with essentially no adverse effects on cell survival or cellular mRNA or total cellular RNA synthesis. Further, these compounds by themself have been tested in humans. Thus, it is believed that the combinations will have utility in inhibiting the progression of an HIV infection and other retroviral infections in cells and in a human including utility in extending the latency of an HIV infection in a human.

In general for the treatment of immunodeficiency infections, for example an HIV or FIV infection, more preferably, an HIV infection, a suitable effective dose of one or more compounds of the combination will be in the range of 0.4 to 100,000 µg per kilogram body weight of recipient per day, preferably in the range of 1 to 10,000 µg, still more preferably in the range of 5 µg to 5000 µg per kilogram body weight per day. The desired dose is suitably administered once or several more sub-doses administered at appropriate intervals throughout the day, or other appropriate schedule. These sub-doses may be administered as unit dosage forms, for example, containing 0.1 to 1000 µg, preferably 5 to 500 µg. These dosages will be lower than that of either compound by itself. For example, one could administer about 40–250 mg of pentoxifylline thrice daily in combination with 40–250 mg of Ro 24-7429. Preferably, the combined amount will be less than 400 mg thrice daily, still more preferably, less than about 350 mg, even more preferably less than about 250 mg, and most preferably less than about 200 mg.

Administration of the compounds of the invention may be by any suitable route including oral, rectal, nasal, topical (including buccal and sublingual), vaginal and parenteral (including subcutaneous, intramuscular, intravenous and intradermal) with oral or parenteral being preferred. It will be appreciated that the preferred route may vary with, for example, the condition and age of the recipient.

The administered ingredients may be used in therapy in conjunction with other medicaments such as reverse transcriptase inhibitors such as dideoxynucleosides, e.g., zidovudine (AZT), 2',3'-dideoxyinosine (ddI) and 2',3'-dideoxycytidine (ddC), protease inhibitors and other agents such as 9-(2-hydroxyethoxymethyl)guanine (acyclovir), interferon, e.g., α-interferon, interleukin II, and phosphonoformate (Foscarnet) or in conjunction with other immune modulation agents including bone marrow or lymphocyte transplants or other medications such as levamisol or thymosin which would increase lymphocyte numbers and/or function as is appropriate. Because many of these drugs are directed to different targets, e.g., reverse transcription, it is anticipated that further advantages will be obtained by this combination.

Similarly, the present compounds may be effective when the above-described drugs are not or are no longer effective. For example, the combination of compounds of the present invention can be used in cells that are resistant to reverse transcriptase inhibitors such as AZT, ddI and ddC. For instance, the combination of compounds, can be used to block HIV-1 LTR directed expression in an AZT resistant strain of HIV-1. Accordingly, the present invention can be used therapeutically in an individual as that individual develops resistance to drugs that act on different targets such as AZT, ddI, ddC, etc. It is expected that the present invention can be used for treatment of HIV-1 infected individuals who develop resistance to any drug that targets a different state in the viral life cycle than the present compounds.

While the combination may be administered alone, they also may be present as part of a pharmaceutical composition. The compositions of the invention comprise at least one combination of compounds together with one or more acceptable carriers, e.g., liposomes, and optionally other therapeutic ingredients, including those therapeutic agents discussed supra. The carrier(s) must be "acceptable" in the sense of being compatible with the other ingredients of the formulation and not deleterious to the recipient thereof.

The compositions include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g., tablets and sustained release capsules, and in liposomes and may be prepared by any methods well known in the art of pharmacy.

Such methods include the step of bringing into association the ingredients to be administered with the carrier which constitutes one or more accessory ingredients. In general, the compositions are prepared by uniformly and intimately bringing into association the active ingredients with liquid carriers, liposomes or finely divided solid carriers or both, and then if necessary shaping the product.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing water, Molded tablets may be made by molding in a suitable machine a mixture of the powdered compound moistened with an inert liquid diluent. The tablets may optionally be coated or scored and may be formulated so as to provide slow or controlled release of the active ingredient therein.

Compositions suitable for topical administration include lozenges comprising the ingredients in a flavored base, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Compositions suitable for topical administration to the skin may be presented as ointments, creams, gels and pastes comprising one or more combination of the compounds of formula (I) and a pharmaceutically acceptable carrier. A suitable topical delivery system is a transdermal patch containing the ingredient to be administered.

Compositions suitable for rectal administration may be presented as a suppository with a suitable base comprising, for example, cocoa butter or a salicylate.

Compositions suitable for nasal administration wherein the carrier is a solid include a coarse powder having a particle size, for example, in the range 20 to 500 microns which is administered in the manner in which snuff is taken, i.e., by rapid inhalation through the nasal passage from a container of the powder held close up to the nose. Suitable formulations wherein the carrier is a liquid, for administration, as for example, a nasal spray or as nasal drops, include aqueous or oily solutions of the active ingredient.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tables of the kind previously described.

It should be understood that in addition to the ingredients particularly mentioned above, the formulations of this invention may include other agents conventional in the art having regard to the type of formulation in question, for example, those suitable for oral administration may include flavoring agents.

All documents mentioned herein are incorporated herein by reference.

The present invention is further illustrated by the following Examples. These Examples are provided to aid in the understanding of the invention and are not to be construed as limitations thereof.

General Methods

The following reagents and procedures were employed as specified in the examples.

Cells. Jurkat, $CD4^+$ T lymphocytes were maintained in tissue culture medium RPMI 1640 supplemented with 10% fetal bovine serum at 37° C. in an atmosphere of 5% $CO_2$ and 95% air.

Drugs and Reagents. Ro24-7429 (7-chloro-N-methyl-5-(1H-pyrrol-2-yl)-3H-1,4-benzodiazepin-2-amine) was obtained from Hoffman-La Roche, Nutley, N.J. Pentoxifylline (PTX) was obtained from Hoechst-Roussel Pharmaceuticals, Inc., Somerville, N.J. 4-β-phorbol-12-β-myristate acetate (PMA), DEAE-dextran, and acetyl CoA were obtained from Sigma Chemical Co., St. Louis, Mo. Tumor necrosis factor-α (TNF-α) was obtained from Genzyme Corp., Boston, Mass. $^{14}$C-Chloramphenicol was obtained from Du Pont New England Nuclear Corp. The complementary strands of the oligonucleotide (SEQ ID NO 1:5'-TCGACAGGGACTTTCCGAGAG 3:) containing the NF-κB motif (bold faced) were custom synthesized by standard procedures in the central facilities of the Dana-Farber Cancer Institute.

Plasmids. The expression plasmids carrying the HIV-1 LTR with wild type (pHIV-1 LTR-CAT) or mutated (pHIV-1 LTR-mut-NF-κB-CAT) NF-κB motifs fused to the reporter gene, chloramphenicol acetyl transferase (CAT), constructed by the procedure of Nabel and Baltimore [Nabel, G. J., et al., Nature 326:711–713 (1987)], were obtained from Dr. G. Nabel of Howard Hughes Medical Center. The Tat-expressing plasmid pSV-Tat and the plasmid carrying a mutation in the tar element (pHIV-1LTR-mut-tar-CAT) as described in [Rosen, C. A., et al., *Cell* 41:813–823 (1985)] were obtained from Dr. J. Sodroski of the Dana-Farber Cancer Institute.

Electrophoretic Mobility Shift Assay (EMSA). NF-κB binding activity in the nuclear extracts of cells was measured by EMSA as described [Fried M., et al., *Nucleic Acids Res.* 9:6505–6525 (1981)]. Nuclear extracts were prepared according to the method of Diagnam, et al. [[Dignam, J. D., et al., *Nucleic Acids Research* 11:1475–1489 (1983)]. The complementary strands of the synthetic oligonucleotide carrying the NF-κB motif were annealed and labeled with $^{32}$P-dCTP [Ausubel, F. M., et al., Current Protocols in Molecular Biology, Greene Publishing Assoc., John Wiley and Sons]. Equal amounts of nuclear proteins from control and treated cells were incubated with the $^{32}$P-NF-κB-oligonucleotide probe (approximately 20–30,000 cpm) at room temperature and subjected to EMSA as described in (Biswas, D. K., et al., *J. Acquir. Immun. Defic. Syndr.* 6:778–786 (1993)]. The NF-κB binding activity was quantitated by densitometric scanning of the specific autoradiographic band in an LKB 2222-020 Ultrascan XL Laser Densitometer (LKB Instruments, Houston, Tex., USA) and subsequent integration of the surface area under each peak. The binding activity (numerals on the Y axis) represents the relative intensity of the quantifitated autoradiographic signals relative to the control.

Transient Transfection and Measurement of Chloramphenicol Acetyl Transferase Activity Jurkat cells ($10^6$ cells/ml) were grown in 150 mm plates in 25 ml tissue culture medium as specified above for 24–30 hours. Cells were pelleted and resuspended in 10 ml of pre-equilibrated sterile transfection medium [Somapayrac, L. M., et al., *Proc. Natl. Acad. Sci. USA* 78:7575–7578 (1981)] containing indicated amounts of specific plasmids and sonicated salmon sperm DNA (carrier) to a total of 20 μg per transfection and were incubated at 37° for one hour. Cells were then subjected to DMSO shock [Biswas, D. K., et al., supra] for 5 minutes, washed and resuspended in complete medium. The transfected cells were then grown for an additional 48–72 hours as indicated in the discussions of the respective figures, under conditions described above. Cell extracts were prepared and CAT activity in a specific amount was measured as described previously (Biswas, D. K., et al., supra). The radioactivity (cpm) in the unreacted $^{14}$C-chloramphenicol (CAP) and in the fractionated $^{14}$C-CAP derivatives were determined by scanning the TLC paper in a Betascope 603 Blot Analyzer, Betagen Corp., Waltham, Mass. CAT activity is expressed as percent $^{14}$C-CAP derivatives produced per hour by the specified amount of cell extract protein.

Inhibition of NF-κB Binding and Down-Regulation of HIV-1 LTR-Driven CAT Gene Expression In Jurkat Cells Jurkat cells were grown as described above. The cells were treated with the indicated concentrations of PTX and/or PMA for 16 hours. FIG. 1 shows the binding activity of NF-κB in the nuclear extracts (10 μg protein) of control and treated cells as described above. The binding activity was quantitated by densitometric scanning of the autoradiographic band designating the specific DNA/protein interaction as described by [Biswas, D. K., et al, supra].

Figure 2:
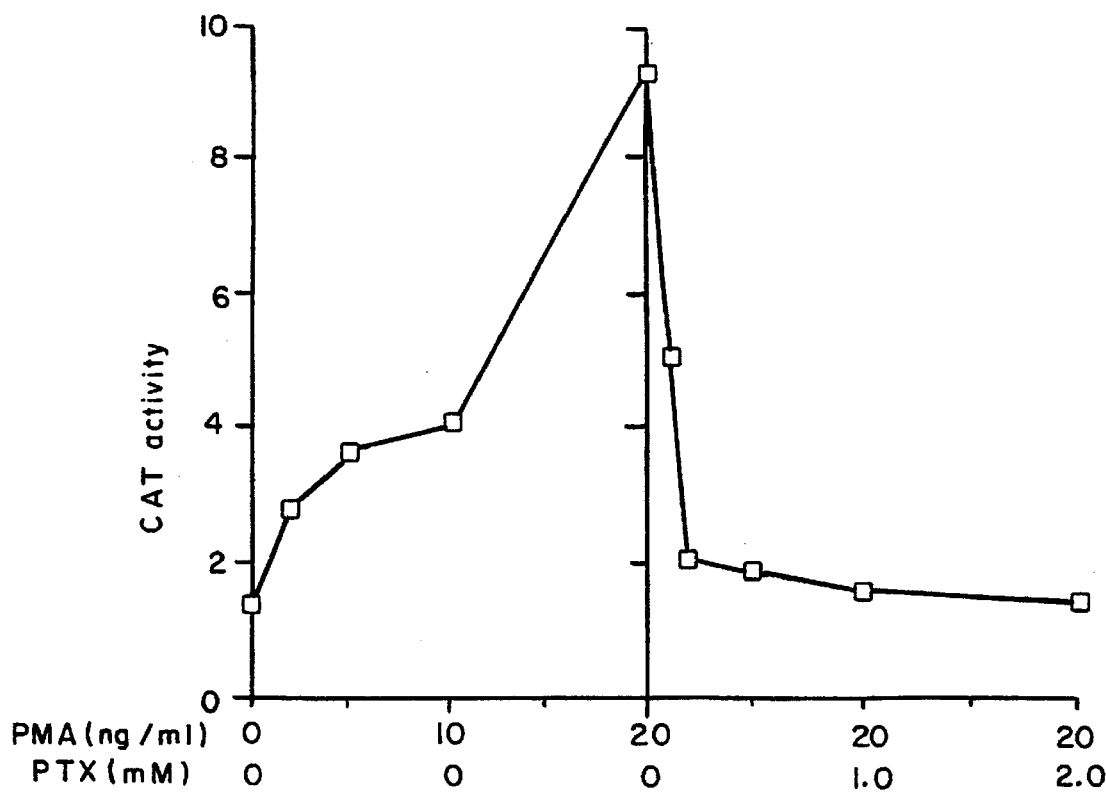
FIG. 2 shows CAT activity in control and treated cells.

FIG. 2 shows the level of CAT activity in extracts of control and treated cells transfected transiently with the fusion gene plasmid, pHIV-1 LTR-CAT [Nabel, G. J., et al., Nature 326, supra] by the DEAE dextran procedure [Somapayrac, L. M., et al., Proc. Natl. Acad. Sci. USA 78:7575–7578 (1981)]. CAT activity is expressed as percent $^{14}$C-CAP derivatives produced per hour in the presence of 10 μg protein of the cell extract. The results shown in the figure are one of three repetitions of this experiment.

Effect of PTX or RO24-7429 On the Individual Action of Tat or NF-κB

Figure 11:
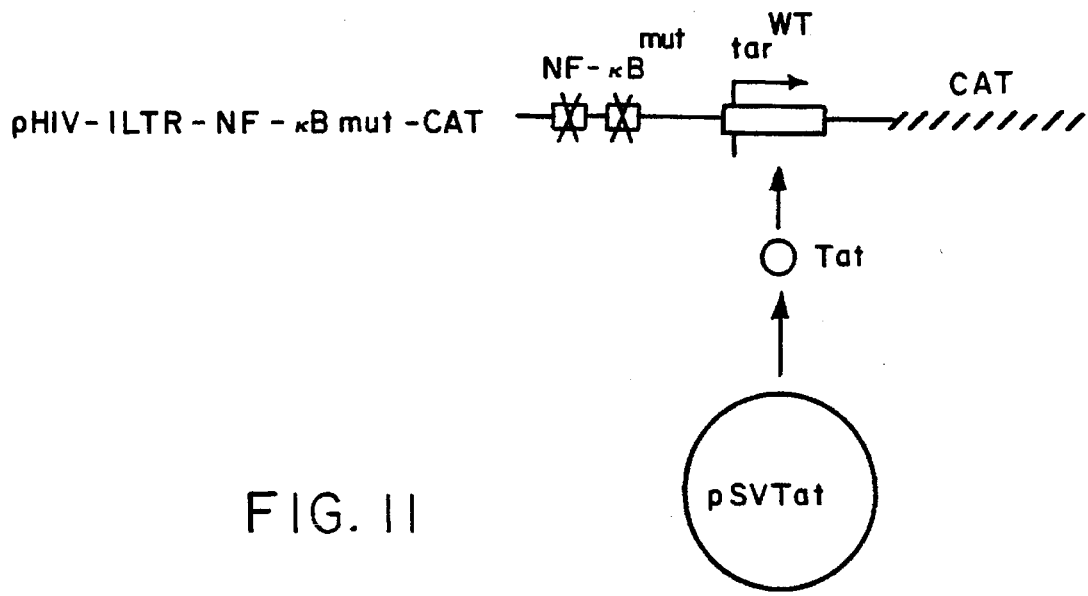
FIG. 11 is a schematic of plasmids pHIV-1 LTR-NF-κB-mutCAT and pSVtat.
Figure 12:
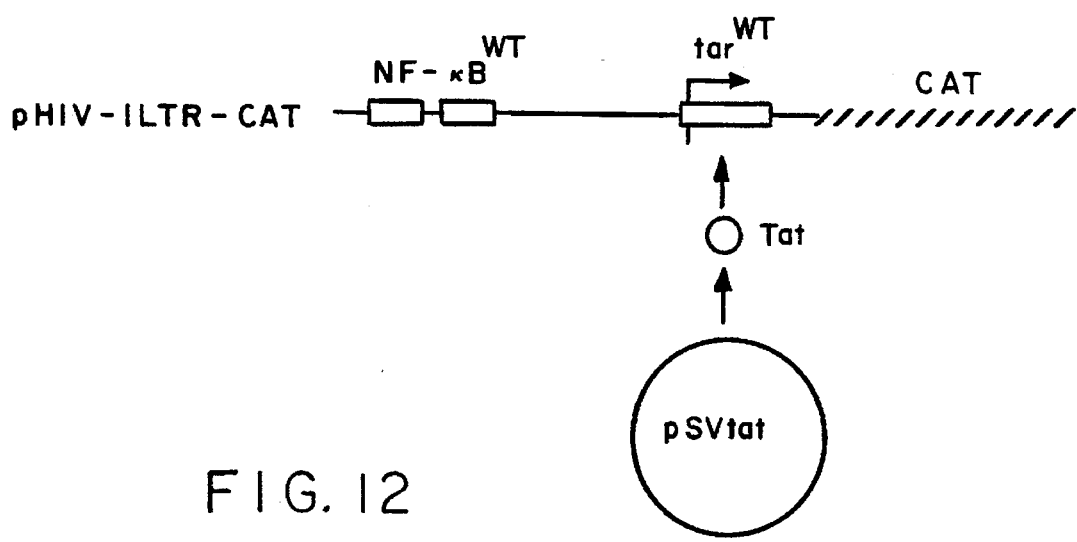
FIG. 12 is a schematic of plasmids pHIV-1 LTR-CAT and pSVtat.

To measure tat activity, cells were co-transfected with the tat-expression plasmid, pSV-tat (5 μg) and the plasmid pHIV-1 LTR-mut NF-κB-CAT (7) (5 μg) as shown in the FIGS. 11 and 12. The concentrations of the drugs and plasmids are tabulated below the bar graph in FIG. 3. The presence or absence (+ or −) of the specific agents at the indicated concentrations are shown. The first bar graph on the left shows CAT activity in the extracts of cells transfected only with pHIV-1 LTR-NF-κB-mut-CAT plasmid with mutated (mut) NF-κB sites, in the absence of tat. The details of the transfection, preparation of cell extracts and measurement and quantitation of CAT activity were the same as described above. Cells were treated with either PMA (20 ng/ml) or PTX (1 mM) or with both for the last 18 hours and with RO24-7429 for the last 48 hours of the 72-hour transfection period. WT indicates the presence of wild type motifs in the LTR sequence in the indicated fusion plasmid.

The action of NF-κB was measured by transfection of cells with fusion plasmid pHIV-1 LTR-CAT carrying the wild type (WT) NF-κB motifs (indicated in FIG. 12 in the absence of tat. The treatments with different agents are indicated in the table below the bar graph as FIG. 4. The first bar graph on the left represents CAT activity in extracts of cells transfected with the plasmid containing the mutated (mut) NF-κB motifs. The results in the figure show one of four repetitions of this experiments.

NF-κB and Tat-Induced Super Activation of HIV-1 LTR

Figure 5:
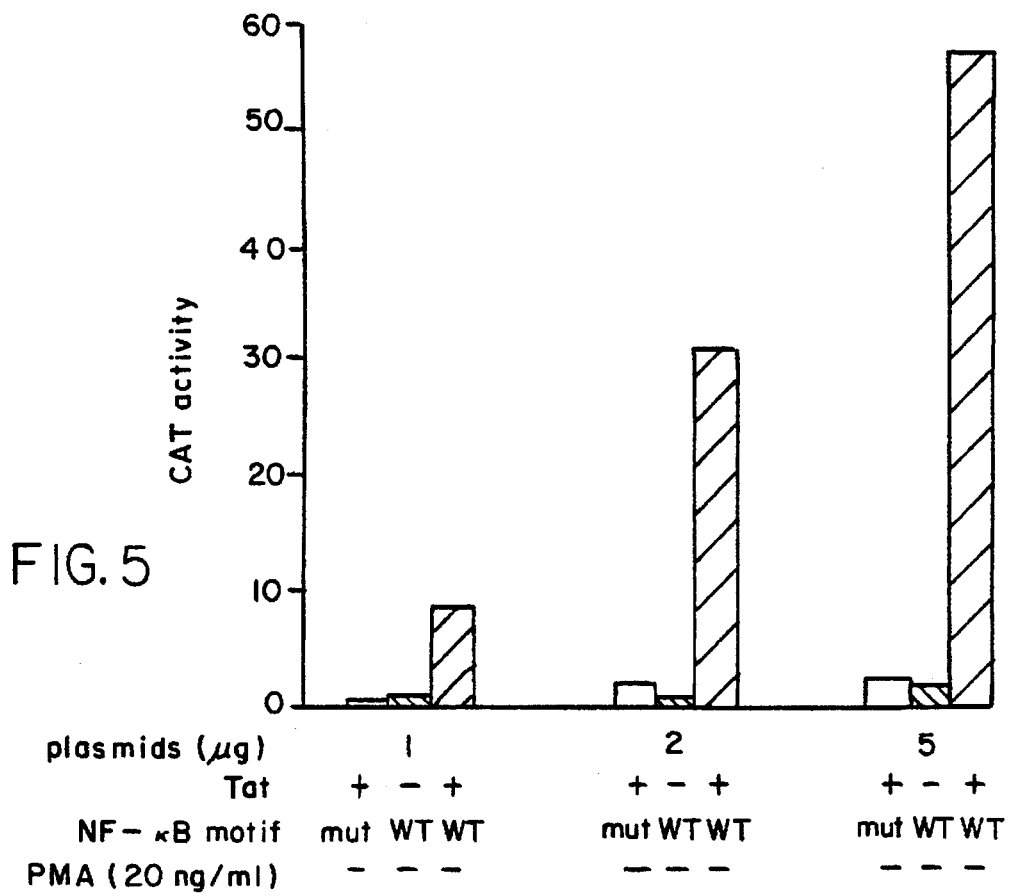
FIG. 5 shows the effect of NF-κB and tat on HIV-1 LTR in the absence of PMA.

Cells were transfected with the concentrations of the plasmid pHIV-1 LTR-CAT alone (containing either mutant or wild-type NF-κB motifs) in the amounts indicated in FIG. 5 to measure the individual action of NF-κB, with indicated concentrations of the plasmid pSVtat alone to measure the individual action of tat, or cotransfected with both plasmids to study the influence of NF-κB and tat combined. Treatment of cells in the presence or absence (+ or −) of PMA (20 ng/mL) or PTX 9 (1 mM), or in the presence of both compounds together are shown. Preparation of cell extracts and assay and quantitation of CAT activity were the same as described above. The figures show plasmid concentration-dependent super-activation of HIV-1 LTR in the absence (FIG. 5) or presence (FIG. 6) of PMA. The results in the figures show one of three repetitions of this experiment.

Figure 7:
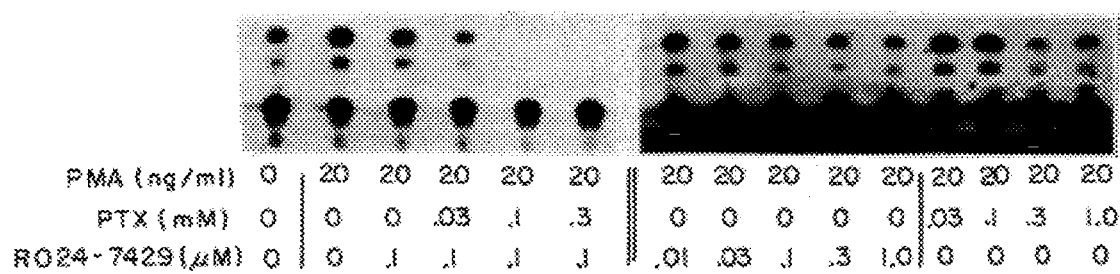
FIG. 7 shows the effect of pentoxifylline and RO24-7429 on NF-κB and tat activation of an HIV-1 LTR.

Combined Effect of PTX and RO24-7429 On NF-κB and Tat-Induced Superactivation of HIV-1 LTR Cells were cotransfected with 2 μg each of the plasmids pHIV-1 LTR-CAT and pSV-tat under conditions described with respect to FIG. 2. Cells were always treated with PMA (20 ng/ml) for the last 18 hours of the 72-hour transfection period. Cells were also treated with RO24-7429 for the last 48 hours and/or PTX for the last 18 hours of the 72-hour transfection period. The concentrations of the drugs are as indicated in FIG. 7. At the end of the transfection period cell extracts were prepared and CAT activity in the extracts (5 μg protein) was measured and quantitated as described above. The left half of the figure shows the effect of combination of the two drugs (constant 0.1 μM RO24-7429 with 0.03–0.3 mM PTX). The right half shows the effects of the drugs when added alone at the indicated concentrations.

Figure 8:
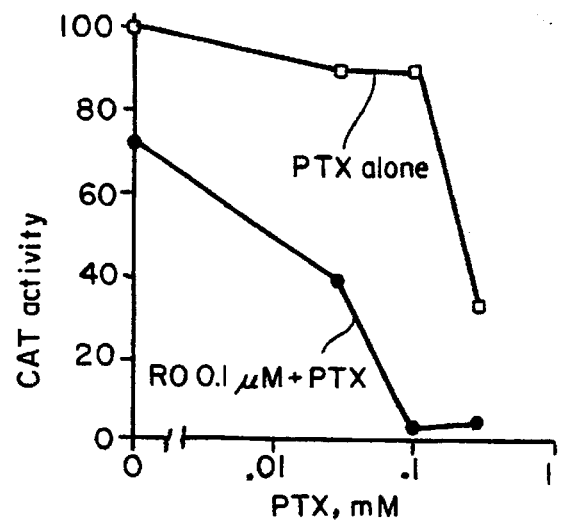
FIG. 8 shows the quantitation of CAT activity data as shown in FIG. 7.
Figure 9:
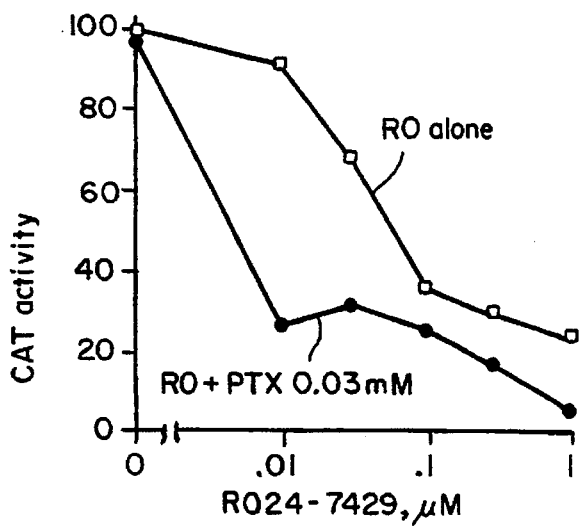
FIG. 9 shows the quantitation of CAT activity in PMA stimulated and transfected cells treated with varying concentrations of RO24-7429 alone or in the presence of pentoxifylline.
Figure 10:
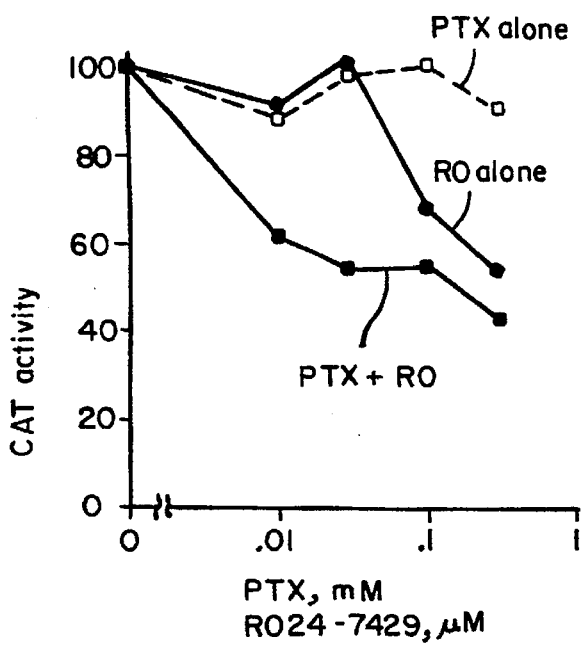
FIG. 10 shows quantitation of CAT activity in cells treated with increasing concentrations of pentoxifylline and RO 24-7429 alone or in combination.

Concentration-Dependent Potentiation of Inhibitory Action of One Drug By the Other Cell growth conditions, transfection, PMA treatment, assay and quantitiation of CAT activity were the same as described above. FIG. 8 shows the quantitation of CAT activity data as shown in FIG. 7. Cells were treated with the indicated concentrations of PTX alone or in the presence of (constant) 0.1 μM RO24-7429. CAT activity in PMA-stimulated cell extract under the influence of both transactivators in the absence of any drugs was designated as 100 in FIGS. 8–10. CAT activity in the presence of 0.1 μM RO24-7429 alone was 75. FIG. 9 shows the quantitation of CAT activity in PMA stimulated andd transfected cells treated with indicated concentrations of RO24-7429 alone or in the presence of (constant) 0.03 mM PTX. CAT activity in the presence of 0.03 mM PTX alone was 97. FIG. 10 shows quantitation of CAT activity in extracts of cells treated with increasing concentrations of either drug alone or in combination.

PTX Inhibits the Interaction of NF-κB With Its Motif and Down-Regulates HIV-1 LTR-Driven Reporter Gene Expression in Jurkat Cells We previously found that PTX inhibits both NF-κB interaction with its motif and HIV-1 LTR-driven reporter gene expression in human embryo kidney cells. These cells, however, are not the natural target of the virus [Biswas, D. K., et al., supra], so the experiments were repeated in a human T lymphoid cell line. Results shown in FIGS. 1 and 2 demonstrate a similar pattern of stimulation by PMA of NF-κB interaction with its motif (FIG. 1) and HIV-1 LTR-driven reporter gene expression (FIG. 2) in the transiently transfected Jurkat CD4$^+$ T cells. Treatment of these stimulated Jurkat cells with PTX showed concentration-dependent inhibitions of the NF-κB-specific DNA/protein interaction and HIV-1 LTR-driven reporter, CAT gene expression.

Figure 3:
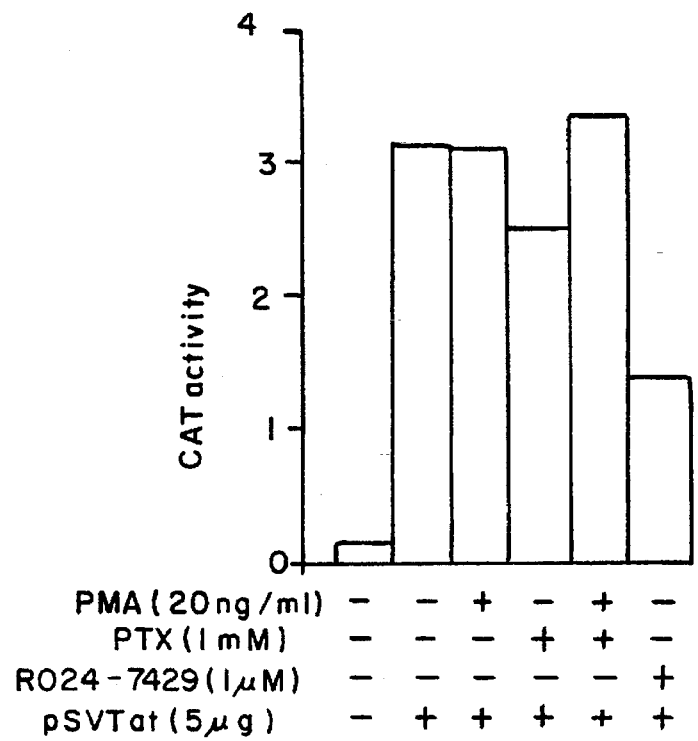
FIG. 3 shows the effect of various compounds on tat activity.
Figure 4:
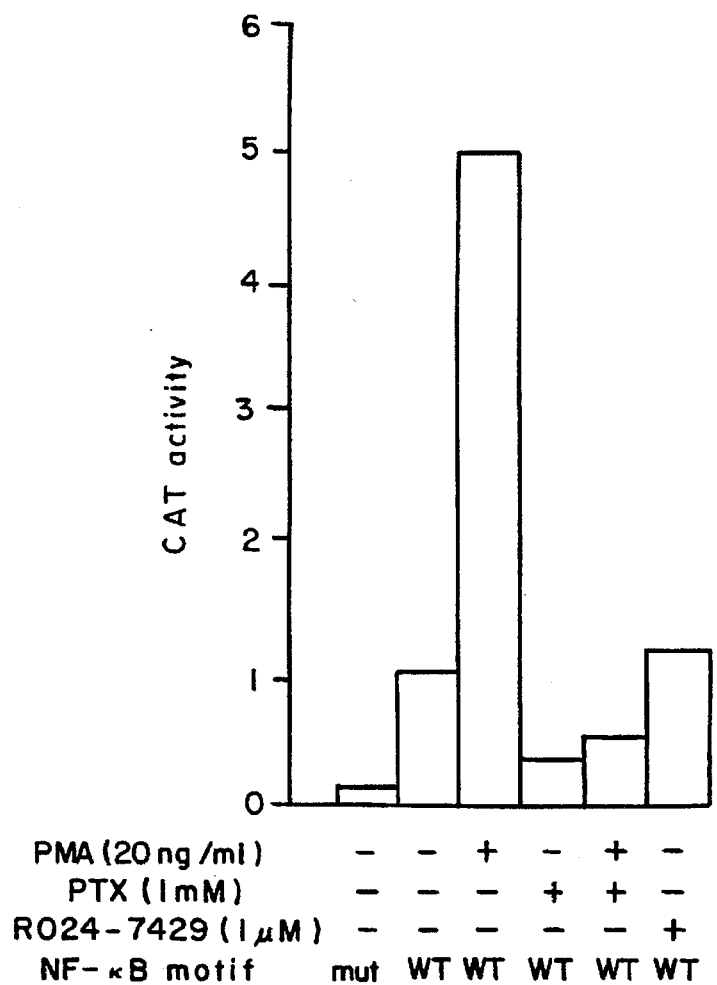
FIG. 4 shows NF-κB action by transfection of cells with the fusion plasmid pHIV-1 LTR-CAT in the absence of tat.

The tat-mediated stimulation of gene expression was examined by transfection of Jurkat cells with a tat-produced expression vector pSV-tat, cotransfected with a plasmid construct containing mutated NF-κB motifs (pHIV-1 LTR-mut-NF-κB-CAT) [Nabel, G. J., et al., Nature 326, supra]. This plasmid provides the tar element, the site of interaction of the tat protein. Because NF-κB binding sites are mutated, trans-activation of the HIV-1 LTR by NF-κB was eliminated in this assay system, thus only tat-mediated activation of the HIV-1 LTR, referred to herein as tat action, is determined. This activation is dependent on the concentration of the input tat-expression plasmid, pSV-tat. Cells transfected with a plasmid carrying a mutated tar element (pHIV-1 LTR-mut-tar-CAT) did not respond to pSV-tat suggesting that the level of CAT activity detected in transfection studies with wild type tar element was a result of tar/tat interaction. Treatment of tat-expressing cells with PMA (FIG. 3) or TNF-α did not further enhance the basal level of tat-induced HIV-1 LTR-driven reporter gene expression. PTX (1 mM) inhibited the basal level NF-κB-mediated activation (FIG. 4) but did not significantly alter the tat-mediated activation of HIV-1 LTR (FIG. 3). In contrast, the tat-inhibitor RO24-7429 inhibited tat action (FIG. 3) but not basal level NF-κB action (FIG. 4).

Figure 6:
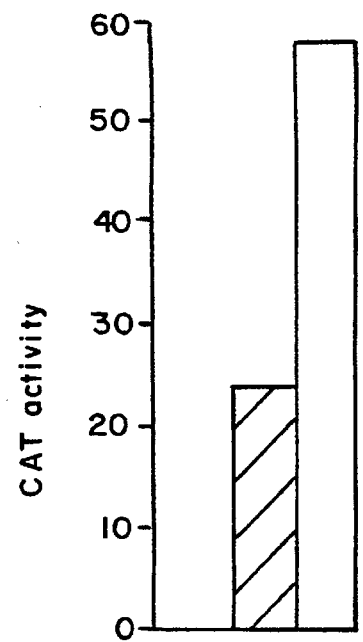
FIG. 6 shows the effect of NF-κB and tat on HIV-1 LTR in the presence of PMA.

The combined action of the two trans-activators, NF-κB and tat, on the level of HIV-1 LTR-driven reporter gene expression was examined in Jurkat cells. Cells were cotransfected with several amounts of both the fusion gene construct pHIV-LTR-CAT carrying the wild type NF-κB and tar elements and the tat-expressing plasmid pSV-tat, thereby providing the cells with functional systems for the simultaneous action of both the trans-activators. Results presented in FIG. 5 demonstrate that the level of CAT gene expression was dependent on the amounts of the input plasmids. This super-activation of HIV-1 LTR in the presence of both NF-κB and tat was 10- and 60-fold higher than was detected in the presence of either tat or wild-type NF-κB motifs alone, respectively, suggesting a concerted action of these two trans-activators in the regulation of viral gene expression. PMA (20 ng/ml) further elevated the NF-κB and tat-induced super-activation (FIG. 6).

The multifactorial concerted activation of HIV-1 LTR was studied in PMA-treated cells, which provide sufficient active NF-κB. The viral protein tat was generated by transfection of PMA treated cells with the expression vector pSV-tat. NF-κB/tat-induced super-activation was inhibited by RO24-7429, an inhibitor of tat (IC$_{50}$, 0.1–0.3 μM), or by PTX, an NF-κB-inhibitor (IC$_{50}$ 0.3–1 mM) (FIG. 7). Most strikingly, concentrations of each of these two inhibitors (0.03–0.1 μM for RO24-7429 and 0.03–0.1 mM for PTX) that did not individually cause significant down regulation of super-activation, strongly inhibited the HIV-1 LTR-driven CAT activity when used in combinations. At these low concentrations the combined effect of the drugs was more than additive, suggesting their synergistic inhibitory influence. Synergy was further demonstrated by treating the cells with a single low concentration of RO24-7429 together with increasing concentrations of PTX (FIG. 7, left side; FIG. 8), vice versa with a single constant concentration of PTX together with increasing concentrations of RO24-7429 (FIG. 9) and by treating the cells with combinations of the drugs at concentrations increasing in parallel (FIG. 10). Variable values for CAT activity at individual drug concentrations either singly or in combination were observed in different experiments. For example, the combination of 0.1 mM PTX and 0.1 μM RO24-7429 strongly inhibited CAT activity in the experiment shown in FIG. 9 but less in the experiment reported in FIG. 10. Similarly, 0.3 mM PTX was more inhibitory in the experiment described in FIG. 9 than FIG. 10. However, it is consistently observed in all these three different experimental conditions that the IC$_{50}$ of each drug in the combination was one log lower than when only one drug concentration was used. Concentrations of drugs in the combination assay at which effective inhibition of HIV-1 LTR activation was observed were not cytotoxic (95% viability), as measured by Trypan Blue exclusion, when the drugs were combined (0.1 mM PTX and 0.1 μM RO24-7429).

Antiviral drugs that target the HIV-1 LTR are attractive because the LTR harbors sites of multifactorial virus specific interplay between cellular and viral factors in regulating the expression of viral genes. Agents that interfere with LTR-mediated gene regulatory function by limiting the availability or activity of trans-activators should adversely affect HIV-1 replication. We have found that concerted interaction of two trans-activators, the cellular factor NF-κB and the viral factor tat, lead to the super-activation of HIV-1 LTR in Jurkat cells. Concerted interplay between cellular and viral factors has been demonstrated in other cell systems [Liu, J., et al., *J. Virol.* 66:3883–3887 (1992); Kammine, J., et al., *J. Virol.* 66:3932–3936 (1992); Kadonaga, J. T., et al., *Science* 242:1566–1570 (1988); Doppler, C., et al., *AIDS Res. Hum. Retro. Viruses* 8:245–252 (1992); Somapayrac, L. M., et al., supra]. The cellular and viral effects of TNF-α, an activator of NF-κB, are increased in a synergistic manner in the presence of tat, which may be explained again on the basis of multifactorial interplay between cellular and viral trans-activators [Somapayrac, L. M., et al., supra]. The molecular mechanism of the NF-κB and tat induced concerted activation of HIV-1 LTR is not clear. The basal level of active NF-κB in unstimulated cells was sufficient to display super-activation of HIV-1 LTR in the presence of tat in cells co-transfected with a plasmid that provides the sites of interaction for simultaneous action of both trans-activators. In PMA-stimulated cells, as expected, the super-activation was exaggerated in the presence of a higher level of active NF-κB.

However, the drugs that target these areas that have been clinically tested have not been entirely successful, and in one instance was viewed as clinically ineffective.

Independent of each other, PTX inhibits NF-κB action [Biswas, D. K., et al., supra] and RO24-7429 inhibits tat action in vitro [Vickers, T., et al., *Nuc. Acids. Research.* 19:3359–3368 (1991); Hsu, M-C, et al., *Science* 254:1799–1802 (1991)], the net result of which is inhibition of HIV-1 LTR activation. Although the two trans-activators, NF-κB and tat, act in concert, neither drug by itself stops the separate effect. Thus, cooperative interaction of the two factors should continue. The results, however, demonstrate a synergistic inhibition of HIV-1 promoter by PTX, the inhibitor of NF-κB, in combination with the tat inhibitor RO24-7429. The concentrations of the drugs in combination that effectively inhibited HIV-1 LTR activation were far below the cytotoxic level. Because very little or no inhibition of either NF-κB or tat actions were noticed when drugs at these low concentrations were used individually, it is anticipated that drug combinations that showed cooperative effect on HIV-1 promoter, will not adversely affect other NF-κB-mediated cellular events.

The results of the three experiments shown in FIGS. 7–10 were nearly a log greater inhibition by the combined drugs than by either alone. However, variable values for individual points were observed from one experiment to another (FIGS. 9 and 10). Although variations of individual values were seen in experiments of this type synergy was always observed. The simple concept that direct interaction between two motifs determines the reporter gene expression does not explain some results. Thus, PTX inhibited NF-κB binding much less than CAT activity (FIG. 1) which might be explained because inhibiting two coordinately-functioning NF-κB motifs should block CAT expression more strongly than binding to one motif. The IC$_{50}$ of RO 24-7429 for PMA-stimulated and PTX inhibited cells was about 0.1 μM whereas, the IC$_{50}$ for inhibition of CAT activity of unstimulated cells by RO24-7429 alone was about 0.1 μM. However, cells not stimulated by PMA but also inhibited by 1 mM PTX showed similarly low NF-κB binding. Thus, PTX may inhibit another factor as well.

It is evident that those skilled in the art given the benefit of the foregoing disclosure may make numerous modifications thereof, and departures from the specific embodiments described herein, without departing from the inventive concepts, and the present invention is to be limited solely to the scope and spirit of the appended claims.

We claim:

1. A method of inhibiting or reducing the expression of genes operably linked to an LTR of an immunodeficiency virus, which comprises administering an effective amount to reduce gene expression of a combination of compounds, wherein the combination comprises a tat inhibitor and an NF-κB inhibitor.

2. A method for treating cells infected with a virus capable of causing an immunodeficiency disease in a human, comprising administering to the cells an effective anti-viral treatment amount of a combination, wherein the combination comprises a tat inhibitor and an NF-κB inhibitor.

3. A method of treating a human having an immunodeficiency disease comprising administering to said human an effective immunodeficiency disease treatment amount of a combination of compounds, wherein the combination comprises a tat inhibitor and an NF-κB inhibitor.

4. A pharmaceutical composition comprising a pharmaceutically-acceptable carrier and an effective anti-viral treatment amount of a combination of compounds, wherein the combination comprises a tat inhibitor and an NF-κB inhibitor.

5. The method of claims 1, 2 or 3, wherein the immunodeficiency virus is the human immunodeficiency virus.

6. The method of claim 5, wherein the human immunodeficiency virus is HIV-1.

7. The method of claims 1, 2, or 3, wherein the tat inhibitor is selected from the group consisting of aryl-(2-pyrryl) ketones and benzodiazepine.

8. The method of claim 7, wherein the compound is 2-glycinamido-5-chlorophenyl (2-pyrryl) ketone, 7-chloro-5-(2)-pyrryl-3H-1,4-benzodiazepin-2(1H)-one or 7-chloro-N-methyl-5-(1H-pyrrol-2-yl)-3H-1,4-benzodiazepin-2-amine.

9. The method of claim 8, wherein the tat inhibitor is 7-chloro-N-methyl-5-(1H-pyrrol-2-yl)-3(H-1,4-benzodiazepin-2-amine.

10. The method of the claims 1, 2, or 3, wherein the combination is selected from xanthine and at least one of the group of compounds consisting of 2-glycinamido-5-chlorophemyl (2-pyrryl) ketone, 7-chloro-5-(2)-pyrryl-3H-1,4-benzodiazepin-2(1H)-one or 7-chloro-N-methyl-5-(1H-pyrrol-2-yl)-3H-1,4-benzodiazepin-2-amine, topotecan, β-lapachone, arryl-β-lapachone and curcumin.

11. The method of claims 1, 2, or 3, wherein the NF-κB inhibitor is N-acetylcysteine, cysteine, or a xanthine.

12. The method of claim 11, wherein the xanthine has the formula

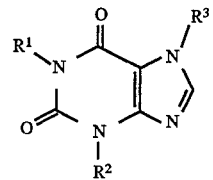

wherein at least one of R$^1$ and R$_3$ is either (a) a branched hydroxyalkyl group of the formula

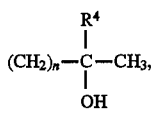

wherein $R^4$ is an alkyl group with 1 to 3 carbon atoms and n is a whole number from 2 to 5, the other $R^1$ or $R^3$ group that may optionally be present is a hydrogen atom or an aliphatic hydrocarbon group $R^5$ with up to 6 carbon atoms, wherein the carbon chain may be interrupted by up to 2 oxygen atoms or may be substituted with a hydroxy or oxo group, or (b) an oxoallyl group of the formula

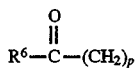

wherein $R^6$ is $C_1$–$C_6$ and p is 2, 3 or 4, the remaining $R^1$ or $R^3$ being as defined above, and $R^2$ is an alkyl group $C_1$–$C_4$.

13. The method of claim 12, wherein the xanthine is selected from the group consisting of 1,3-di-methylxanthine (theophylline), 1-(5-oxohexyl)-3,7-dimethylxanthine (pentoxifylline), 1-(5-hydroxy-5-methylhexyl)-3-methylxanthine) (HWA 138), 7-ethoxymethyl-1-(5-hydroxy-5-methylhexyl)-3-methylxanthine (HWA 448) and 7-propyl-1-(5-hydroxy-5-methylhexyl)-3 methylxanthine (A80 2715).

14. The method of claim 13, wherein the xanthines are selected from the group consisting of pentoxifylline, BL194, HWA 138, HWA 448, and A80-2715.

15. The method of claim 14, wherein the xanthine is selected from the group consisting of HWA 138, and HWA 448.

16. The method of claim 15, wherein the xanthine is pentoxifylline.

17. The pharmaceutical composition of claim 4, wherein the combination is 1-(5-oxohexyl)-3,7 dimethylxanthine and 7-chloro-N-methyl-5-(1H-pyrrol-2-yl)-3H-1,4-benzodiazepin-2-amine.

* * * * *